(12) United States Patent
Strong et al.

(10) Patent No.: US 10,098,794 B2
(45) Date of Patent: Oct. 16, 2018

(54) DISCRETE CORD DELIVERY APPARATUS

(71) Applicant: The Procter & Gamble Company, Cincinnati, OH (US)

(72) Inventors: Kevin Charles Strong, Loveland, OH (US); Evan Joseph Durling, West Chester, OH (US); Jason Matthew Orndorff, Lawrenceburg, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/685,074

(22) Filed: Aug. 24, 2017

(65) Prior Publication Data

US 2017/0348161 A1 Dec. 7, 2017

Related U.S. Application Data

(63) Continuation of application No. 14/307,109, filed on Jun. 17, 2014, now Pat. No. 9,770,372.

(60) Provisional application No. 61/836,452, filed on Jun. 18, 2013.

(51) Int. Cl.
*B65G 53/40* (2006.01)
*A61F 13/34* (2006.01)
*A61F 13/20* (2006.01)

(52) U.S. Cl.
CPC .......... *A61F 13/34* (2013.01); *A61F 13/2085* (2013.01)

(58) Field of Classification Search
None
See application file for complete search history.

(56) References Cited

U.S. PATENT DOCUMENTS

| | | | | |
|---|---|---|---|---|
| 2,634,491 A | * | 4/1953 | McDermott | D01D 10/0454 226/7 |
| 3,241,234 A | * | 3/1966 | Kiefer | B65H 54/88 226/97.4 |
| 3,607,520 A | | 9/1971 | Jones | |
| 3,678,579 A | * | 7/1972 | Slavik | B65H 51/16 226/97.1 |
| 3,857,309 A | * | 12/1974 | Bradley | B26D 5/28 83/13 |
| 3,922,938 A | * | 12/1975 | Hautemont | B65H 51/16 83/100 |
| 4,048,884 A | | 9/1977 | Winn, Jr. | |
| 4,389,774 A | * | 6/1983 | McLaughlin, Jr. | B26D 1/38 242/487.9 |
| 4,655,111 A | | 4/1987 | Blaker | |
| 5,086,679 A | * | 2/1992 | Fletcher | B65H 54/88 83/100 |
| 5,219,185 A | | 6/1993 | Oddenino | |
| 5,836,225 A | | 11/1998 | Molnar | |
| 6,182,332 B1 | | 2/2001 | Jander | |
| 7,011,033 B2 | | 3/2006 | Sargent et al. | |

(Continued)

*Primary Examiner* — William Ray Harp
(74) *Attorney, Agent, or Firm* — Andres E. Velarde

(57) ABSTRACT

An apparatus for delivering a discrete cord having a supply path comprising a fluid flow, a deployed cord supply, a transfer member having a first surface comprising one or more orifices capable of receiving the deployed cord supply, and a cutting apparatus comprising a cutting implement enabled to sever the deployed cord supply to form a discrete cord. The fluid flow directs the deployed cord supply towards the transfer member first surface. The transfer member first surface abuts the cutting apparatus.

17 Claims, 19 Drawing Sheets

(56) References Cited

U.S. PATENT DOCUMENTS

| | | |
|---|---|---|
| 7,628,114 B2 | 12/2009 | Aoyama et al. |
| 7,673,573 B2 | 3/2010 | Kondo et al. |
| 7,677,189 B2 | 3/2010 | Kondo et al. |
| 8,961,485 B2 | 2/2015 | Middlebeek et al. |
| 9,211,217 B2 | 12/2015 | Tomsovic |
| 9,770,372 B2 * | 9/2017 | Strong ................ A61F 13/2085 |
| 9,782,908 B2 * | 10/2017 | Durling ................ B26D 7/0658 |
| 2003/0131456 A1 | 7/2003 | Rajala |
| 2012/0109095 A1 | 5/2012 | Middlebeek |
| 2014/0352129 A1 * | 12/2014 | Strong ................ A61F 13/2085 |
| | | 29/428 |
| 2014/0367404 A1 | 12/2014 | Strong et al. |
| 2015/0000482 A1 | 1/2015 | Strong et al. |
| 2015/0000490 A1 | 1/2015 | Durling et al. |

* cited by examiner

DISCRETE CORD DELIVERY APPARATUS

FIELD OF INVENTION

The present disclosure relates to an apparatus enabled to deliver a discrete cord to a transfer member, and more particularly, to an apparatus enabled to deliver a discrete cord to a transfer member utilizing fluid flow in a supply path.

BACKGROUND OF THE INVENTION

Withdrawal cords are commonly sewn onto tampons to help ease in the removal of the tampon from the vaginal cavity. Typically, during the manufacturing process, a continuous cord is sewn onto multiple pledgets thereby connecting the pledgets. The pledgets may be spaced on a conveyor connected by the continuous cord. The amount of cord between two pledgets may comprise the amount of cord that is not sewn to the pledget, which represents the graspable portion of a withdrawal cord. The cord is then cut between pledgets in a separate process; leaving a portion of the cord attached to the pledget prior to the location of the cut and portion of the cord attached to a pledget after the location of the cut. The typical process also sews the cord onto the entire longitudinal length of the pledget. This leads to unnecessary sewing that utilizes excess sewing thread and cord. This process also creates inefficiency because the conveyor must space the pledgets to account for the desired length of cord between pledgets.

The typical process ideally cuts the cord without cutting any of the pledgets. However, often, one or more pledgets are partially cut when cutting the cord. This leads to irregular pledgets that are discarded because they do not meet the product target.

Therefore, it would be desirable to provide an apparatus for delivering a discrete cord to a transfer member through a supply path. The transfer member may move the discrete cord to an attachment system capable of attaching a single discrete cord to a pledget. This allows for a reduced sewing requirement per pledget while possibly increasing the pledget production rate.

SUMMARY OF THE INVENTION

An apparatus for delivering a discrete cord is disclosed. The apparatus having a supply path comprising a fluid flow, a deployed cord supply, a transfer member having a first surface comprising one or more orifices capable of receiving the deployed cord supply, and a cutting apparatus comprising a cutting implement enabled to sever the deployed cord supply to form a discrete cord. The fluid flow directs the deployed cord supply towards the transfer member first surface. The transfer member first surface abuts the cutting apparatus. The transfer member comprises a plurality of segments forming a closed chain.

An apparatus for delivering a discrete cord is disclosed. The apparatus having a supply path comprising a fluid flow, a deployed cord supply, a transfer member having a first surface comprising one or more orifices capable of receiving the deployed cord supply, and a cutting apparatus comprising a cutting implement enabled to sever the deployed cord supply to form a discrete cord. The fluid flow directs the deployed cord supply towards the transfer member first surface. The transfer member first surface abuts the cutting apparatus. The transfer member comprises a body with an aperture enabled to reciprocate along a line or arc that moves the aperture through the fluid flow.

An apparatus for delivering a discrete cord is disclosed. The apparatus having a supply path comprising a fluid flow, a deployed cord supply, a transfer member having a first surface comprising one or more orifices capable of receiving the deployed cord supply, and a cutting apparatus comprising a cutting implement enabled to sever the deployed cord supply to form a discrete cord. The fluid flow directs the deployed cord supply towards the transfer member first surface. The transfer member first surface abuts the cutting apparatus. The transfer member comprises a plurality of segments forming a rigid structure.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
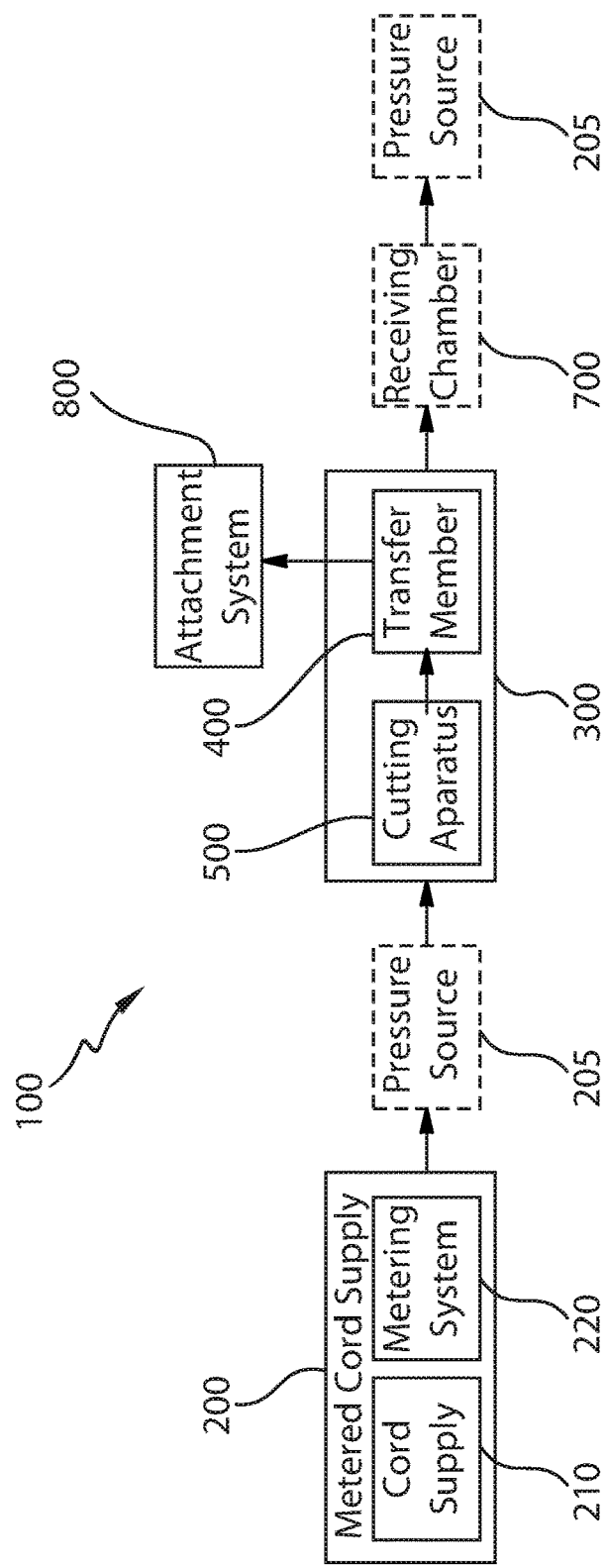
FIG. 1 is a simplified flowchart representation of the apparatus.

The following definitions may be useful in understanding the present disclosure.

"Compressed" refers herein to pressing or squeezing together or otherwise manipulating the size, shape, and volume to obtain a generally elongated absorbent member having a vaginally insertable shape.

"Cross direction" (CD) refers herein to a direction that is not parallel with, and usually perpendicular to, the machine direction.

"Fluid flow" refers herein to the flow of a medium. The path taken by the medium defines a fluid flow path.

"Machine direction" (MD) refers herein to the direction of material flow through a process. In addition, relative placement and movement of material can be described as flowing in the machine direction through a process from upstream in the process to downstream in the process.

As used herein, "negative" pressure refers to less than atmospheric pressure.

The terms "pledget" and "tampon pledget" refer herein to a construction of absorbent material prior to the compression of such construction into a tampon as described below. A pledget may be in the form of a chevron.

Tampon pledgets are sometimes referred to as tampon "blanks" or "softwinds," and the term "pledget" is intended to include such terms as well.

As used herein, "positive" pressure refers to greater than atmospheric pressure.

As used herein, a "substrate" relates to a material or a combination of materials that create a first plane and a second plane, opposite the first plane, such as, for example, a pledget, a plate, a sheet of glass, and a sheet of material. The substrate can comprise, for example, cellulose based materials, fibrous materials, metals, glass, silicate materials, thermoplastics, and thermoset plastics.

The term "tampon," as used herein, refers to any type of absorbent member that is inserted into the vaginal cavity or other body cavities for the absorption of fluid therefrom. Typically, tampons are constructed from a generally elongated absorbent member that has been compressed or formed into a vaginally insertable shape.

The term "vaginal cavity" refers herein to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of the vestibule. The external visible genitalia generally are not included within the term "vaginal cavity" as used herein.

The term "volume" refers herein to the volume of the fibers and the void space within the pledget. Volume is measured by the multiplication of the length by the width by the thickness of the pledget.

The present disclosure relates to an apparatus for delivering a discrete cord to a transfer member utilizing fluid flow in a supply path. Once delivered, an orifice on the transfer member may move out of a fluid flow and deliver the discrete cord to an attachment system. The discrete cord may be attached onto a substrate, such as, for example, a pledget. The apparatus may be timed with a conveyor that delivers the pledgets such that each discrete cord is delivered to a pledget.

In an exemplary configuration, a metered cord supply may advance a deployed cord supply to a supply path. The supply path is fluidly connected to the metered cord supply and comprises a transfer member, a transfer tube and a cutting apparatus. The transfer member comprises a first surface, a second surface, and an orifice in the transfer member first surface. The supply path contains a fluid flow capable of carrying a deployed cord supply. The fluid flow may be created by positive pressure, negative pressure, or combinations thereof. The fluid flow is directed to deliver the deployed cord supply to the transfer member abutting the cutting apparatus. In such an exemplary configuration, the cutting apparatus may be configured to cut a set amount of cord once the deployed cord supply enters the orifice in the transfer member. Cutting the deployed cord supply creates a discrete cord. At least a portion of the discrete cord is within the orifice of the transfer member.

In an exemplary configuration, a metered cord supply advances a deployed cord supply to a supply path. The supply path is fluidly connected to the metered cord supply and comprises a transfer member, a transfer tube and a cutting apparatus. The transfer member comprises a first surface, a second surface, and an aperture through the transfer member connecting the first surface to the second surface. The supply path contains a fluid flow capable of carrying a deployed cord supply. The fluid flow may be created by positive pressure, negative pressure, or combinations thereof. The fluid flow is directed to deliver the deployed cord supply to the transfer member first surface abutting the cutting apparatus. In such an exemplary configuration, the fluid flow is created by negative pressure from a vacuum source within a receiving chamber that abuts the second surface of the transfer member. The cutting apparatus may be configured to cut a set amount of cord once the deployed cord supply enters an aperture in the transfer member. Cutting the deployed cord supply creates a discrete cord. At least a portion of the discrete cord is within the aperture of the transfer member.

In an exemplary configuration, a metered cord supply advances a deployed cord supply to a supply path. The supply path is fluidly connected to the metered cord supply and comprises a transfer member, a transfer tube and a cutting apparatus. The transfer member comprises a first surface, a second surface, and an aperture through the transfer member connecting the first surface to the second surface. The supply path contains a fluid flow capable of carrying the deployed cord supply. The fluid flow is created by negative pressure from a vacuum source within a receiving chamber that abuts the second surface of the transfer member. The fluid flow is directed to deliver the metered supply cord to the transfer member first surface abutting the cutting apparatus. The deployed cord supply enters the aperture in the transfer member. A tangible body causes the deployed cord supply to contact the first surface of the transfer member at the same time or before the cutting apparatus cuts the deployed cord supply to form a discrete cord. The transfer member aperture moves out of the fluid flow taking the discrete cord.

The receiving chamber second end wall may comprise an outlet and a tunnel. The receiving chamber outlet deflects the discrete cord, whereby the cord is forced upon the transfer member second surface. The discrete cord second end may conform to the transfer member first surface due to the tangible body.

After exiting the receiving chamber outlet, the discrete cord comes in contact with an attachment system capable of joining the discrete cord to a substrate.

The transfer member, cutting apparatus, and a metering system may work in unison to deliver a discrete cord to each orifice of the transfer member. The transfer member, cutting apparatus, and metering system may work in unison to deliver a discrete cord of any length. Alternatively, the transfer member, cutting apparatus, and metering system may be set to work in unison to deliver a discrete cord at a set rate, such as, for example, to deliver discrete cords to the orifices at any desired pattern, such as, for example, every other orifice. Alternatively, the transfer member, cutting apparatus, and metering system may each be controlled as an individual unit to control discrete cord delivery by speeding up or slowing down one or two units while maintaining the other unit(s) constant. In a configuration, the maximum velocity of the apparatus may be limited by the rate at which the attachment system may attach a discrete cord to a substrate, such as, for example, the rate at which a sewing machine can sew the discrete cord.

The cord delivery system may comprise a cord supply and a metering system. The metering system directs an end of a deployed cord supply into a supply path. The metering system may comprise any metering system suitable for feeding a cord into a system, such as, for example, an apron roll or an omega roll. The metering system may comprise two rolls working in unison to direct the cord to the supply path. The metering system controls the deployed cord supply length delivered to the cutting apparatus. The metering system may be used as a phasing apparatus to control discrete cord position, wherein the cord has a distinguishing feature, such as, for example, a slub or a change in color.

The apparatus comprises a transfer member connected to a cutting apparatus. The cutting apparatus is connected to a transfer tube. The transfer tube is connected to a cord delivery system. The transfer member, cutting apparatus, and the transfer tube form a supply path for the deployed cord supply from the cord delivery system.

The supply path may contain a pressure source that creates a fluid flow directed towards the transfer member. The fluid flow may carry a cord. The fluid flow may comprise any medium capable of carrying a cord, such as, for example, air. The fluid flow may be created by one or more pressure sources that generate fluid movement, such as, for example, a positive displacement pump, a blower, a vane pump, and a venturi device.

The fluid flow may be created by positive pressure, negative pressure, and combinations thereof. Positive pressure may be introduced into the supply path at the inlet of the transfer tube. Positive pressure may be introduced before the metering system provided that the metering system forms part of the fluid flow path. Changes in pressure may be introduced at any point along the supply path provided that the pressure does not contradict the fluid flow direction.

Negative pressure may be created by a vacuum source connected to a receiving chamber abutting the second surface of the transfer member. The fluid flow velocity must exceed the required cord velocity in the supply path. The required cord velocity is determined by the desired length of a discrete cord. The required fluid flow velocity will vary depending on the cord material, the desired length of the discrete cord, and any fluid flow losses or restrictions in the supply path. The fluid flow velocity should not be capable of damaging the supply cord.

Under negative pressure, the fluid flow velocity may be maintained between a vacuum source and the cord delivery system such that the fluid flow velocity exceeds the cord velocity in the supply path by the apertures in the transfer member or by a combination of a hole and the aperture in the transfer member body comprising one aperture. Under negative pressure only, the vacuum should be at least ten inches of water.

To maintain the fluid flow velocity, the supply path should minimize the number of bends, restrictions, and pressure leaks. Bends in the supply path create pressure drops and may increase turbulence at particular portions of the supply path leading to reduced fluid flow velocity. Similarly, any leaks in the supply path will lead to a reduced fluid flow velocity. Leaks may be reduced, if not eliminated, by choosing the appropriate materials so that a seal will exist between the opening to the cutting apparatus and the transfer member and between the transfer member and the receiving chamber. Compatible materials may allow for a constant seal while still allowing the transfer member to bisect the fluid flow without adverse friction. In a non-limiting configuration, the transfer member comprises stainless steel and the cutting apparatus opening and the receiving chamber opening comprise nylon. Similarly, a tight seal should exist between the transfer tube and the cutting apparatus.

Without being bound by theory, it is believed that utilizing a fluid flow allows the cord supply to follow the fluid flow created by the positive or negative pressure into an orifice of the transfer member. This allows for a fluid flow that adapts to the position of the orifice in the supply path. The cord supply comprises a flexible cord that may follow the fluid flow to the orifice within the supply path. Without being bound by theory, it is believed that enabling the flexible cord to follow the fluid flow allows for a faster production of discrete cords. Allowing the flexible cord to follow the fluid flow allows a cord to enter an orifice in the transfer member while moving the transfer member orifice. This may increase the throughput of discrete cords to a transfer member.

The transfer member may comprise any tangible body that is capable of receiving an end of a deployed cord supply, capable of moving the deployed cord supply, capable of moving a discrete cord, and that does not inhibit the fluid flow velocity. The transfer member comprises one or more orifices on the first surface that receive the deployed cord supply first end. The one or more orifices may be, for example, apertures that connect the transfer member first surface to the transfer member second surface or cavities with additional fluid channels that do not restrict the fluid flow, while restricting the first end of the deployed cord supply. In a non-limiting configuration, one or more apertures may each contain an obstruction that prevents the deployed cord supply from crossing the second surface of the transfer member without inhibiting the fluid flow velocity.

In a non-limiting configuration, the transfer member may comprise a unitary body in the form of a ring with a plurality of orifices that are equidistantly spaced along a rim abutting the perimeter of the transfer member and are capable of receiving the deployed cord supply, a closed chain of segments wherein each segment comprises an orifice capable of receiving the deployed cord supply, or a body with one orifice capable of receiving the deployed cord supply and a hole. In a non-limiting configuration, the first surface of the transfer member is proximal to a cutting apparatus and distal to an optional receiving chamber. In a non-limiting configuration, the second surface of the transfer member is proximal to an optional receiving chamber and distal to a cutting apparatus.

The transfer member may comprise a unitary body in the form of a ring with a plurality of orifices in the form of apertures that are equidistantly spaced along a rim abutting the perimeter of the transfer member. The ring comprises a central axis. The transfer member central axis may or may not be vertical or horizontal. The rigid body of the transfer member may be connected to the central axis by one or more spokes.

Alternatively, the transfer member may comprise a closed chain of segments wherein each segment comprises an orifice in the form of an aperture. The closed chain comprises two or more segments connected to each other, to a common axis, or a combination thereof. The transfer member segments move their respective orifices through the fluid flow, receive the discrete cord, and deliver it to the attachment system.

The segments comprise a first surface, a second surface, a front end, a back end, a width defined by the distance between the first surface and the second surface, a height, and a length. The height and length of the segment define a first surface area of the segment on the first surface and a second surface area of the segment on the second surface. The second surface height may be different than the first surface height making the first surface area a different dimension from the second surface area. The segments may be connected in a rigid closed structure, such as, for example, a ring or in a non-rigid closed structure, such as, for example, a closed serpentine chain. The two or more segments are connected such that the front end of a segment is connected to the back end of a second segment. In a rigid body, the one or more segments comprise a rim defined by the first surface area and the second surface area of the segments. The segment comprises an aperture that connects the first surface and the second surface.

The transfer member may comprise a body with one aperture. The body with one aperture has a length which is at least the width of the aperture plus the width of the greater of the two openings abutting the first surface and the second surface of the body. The body with one aperture reciprocates along a line or arc that moves the aperture through the fluid flow. The body with one aperture may comprise an additional hole which connects the first surface of the body to the second surface of the body. The additional hole serves to maintain a fluid flow between the cord supply and the receiving chamber when the aperture is outside the fluid flow.

The transfer member that is a body with one aperture reciprocates along a line or arc that moves the aperture through the fluid flow. The aperture may receive the cord supply at any point wherein the aperture is in the fluid flow. The cutting apparatus cuts the cord supply creating a discrete cord. The aperture moves out of the fluid flow to deliver the discrete cord to the attachment system. The additional hole may maintain the fluid flow while the aperture is outside of the fluid flow.

The transfer member may comprise protuberances that extend from the width of the transfer member between the first surface and the second surface. The protuberances may extend from either width.

The apertures may be between about 4 mm$^2$ and 100 mm$^2$, such as, for example, 50 mm$^2$, 40 mm$^2$, 30 mm$^2$, 20 mm$^2$, and 10 mm$^2$. The apertures may be tapered from a larger opening on the first surface to a smaller opening on the second surface. The large opening on the first surface increases the target for the deployed cord supply. The smaller opening on the second surface increases positional control of the discrete cord first end. Tapering allows increased air flow velocity through the aperture in the small end of the aperture compared to the large end.

In a non-limiting configuration wherein the attachment system is on the second surface of the transfer member, the width of the transfer member may not be greater than the length of the discrete cord. In a non-limiting configuration, the width of the transfer member may not be less than half of the difference between the unsewn cord length and the pitch of the apertures in the transfer member. If the width of the transfer member is less than the cord length minus the pitch of the apertures in the transfer member, a second end of the discrete cord may enter the receiving chamber through the aperture following the aperture containing the first end of the discrete cord. This may cause the same discrete cord to be sewn onto two pledgets.

In a non-limiting configuration, wherein the transfer member comprises a rigid body comprised of segments that rotate about the central axis of the rigid body, the transfer member may be held by three or more support wheels. The three support wheels may be in a triangle configuration. Alternatively, the transfer member may be held by four support wheels in a square configuration. In a non-limiting configuration, the rigid ring of segments may be rotated by a belt which is connected to a drive wheel.

The cutting apparatus comprises a cutting implement enabled to sever the deployed cord supply to form a discrete cord, such as, for example, a rigid knife, a laser, a rotary knife, a flexible knife, a guillotine, or a blade. In an exemplary configuration, a knife is attached to a rotary axis that rotates the knife through the supply path. A pressure surface, such as, for example, a rotating anvil, may be located opposite the knife. The knife may contact the pressure surface, severing the cord supply.

In a non-limiting configuration, the cutting apparatus comprises a volumetric space joining the point at which the knife crosses the supply path and the transfer member. The volumetric space allows for a smooth transition between the point at which the knife crosses the supply path and the opening that abuts the transfer member with minimal increase in cross section area to maintain fluid flow velocity.

The opening is formed by a first edge, a second edge, a top wall connecting the first edge to the second edge, and a bottom wall connecting the first edge to second edge.

If the opening has a length greater than one pitch of the apertures on the transfer member plus one width of the apertures, then the end of a first discrete cord may enter the aperture for the second cord and/or the beginning of the second cord may enter the aperture of the first discrete cord.

The cutting apparatus may comprise an alternative fluid flow path when the knife rotates through the supply path. The alternative fluid flow path ensures that a fluid flow exists when the knife bisects the fluid flow path taken by the deployed cord supply. The alternative fluid flow path may be formed by a gap between the rotary axis for the knife and a casing for the knife. When the knife does not bisect the deployed cord supply fluid flow path, this alternative fluid flow path is blocked by the knife.

When the transfer member comprises more than one segment or is a rigid ring, the cutting apparatus opening may be less than the area of the abutting first surface of a segment of the transfer member or a pitch of the rigid ring and the cutting apparatus opening follows the line of motion of the aperture of the transfer member. The length of the cutting apparatus opening must be greater than the length of the segment.

Alternatively, when using a transfer member body comprising a single aperture, the cutting apparatus opening may be less than the area of the first surface of the transfer member body. The cutting apparatus opening length must be greater than the width of the hole plus the distance between the hole and the aperture.

The transfer tube may comprise an inlet in proximity or abutting the metering system of the cord delivery system and an outlet that is in direct contact with the cutting apparatus. The transfer tube may be made of any material that can sustain a tubular form under the required amount of negative pressure, positive pressure, or combinations thereof, such as, for example, stainless steel and polycarbonate.

The transfer tube may be any suitable diameter, such as, for example, 1 mm to 20 mm, such as, for example, 3 mm, 4 mm, 5 mm, 6 mm, 7 mm, 8 mm, 9 mm, 10 mm, 15 mm. The transfer tube should have the least number of bends possible to reduce the loss of air velocity in the transfer tube.

The metered cord supply comprises a metering system and a cord supply. The metering system may comprise any suitable feed mechanism, such as, for example, an omega roll, an apron roll, or a two roll nip. The metering system controls the rate at which the cord supply is deployed to the supply path. In an exemplary configuration, the metering system comprises an apron roll and a drive wheel.

The cord supply can comprise any suitable material, including for example, cotton, cellulose, rayon, polyolefins such as, for example, polyethylene or polypropylene, nylon, silk, polytetrafluoroethylene, wax, Teflon, or any other suitable materials.

The cord supply may be non-absorbent along at least the location of attachment to the pledget. As used herein, the term "non-absorbent" refers to a structure that does not retain a significant portion of deposited fluid in its structure. The entire cord may be made non-absorbent, if desired. The materials comprising the cord may be inherently non-wettable or hydrophobic, or they may be treated to provide such properties. For example, a coating of wax may be applied to the cord to decrease or eliminate its absorbency. The cord need not necessarily be non-wicking, even if a non-absorbent cord is desired.

The cord supply can be formed by any suitable formation method and in any suitable configuration, such as, for example, one or more cords, strings, finger covers, ribbons, an extension of a material of the device, or combinations thereof.

The cord supply may alternate between a distinguishing feature and a length of plain cord. One discrete cord may be made up of a distinguishing feature and one or more lengths of plain cord. The distinguishing feature may be a slub. The slub may be attached onto the pledget. The length of plain cord may extend beyond the pledget. The length of the slub and the length of the plain cord are predetermined in the cord supply. The cord supply may comprise a continuous cord that alternates between slubs and non-slub portions or lengths of plain cord.

The discrete cord may be any suitable length, such as, for example, between 10 mm and 200 mm, between 20 mm and 150 mm, between 20 mm and 100 mm, 200 mm or less, 150 mm or less, 100 mm or less, such as for example, 90 mm, 80 mm, 70 mm, 60 mm, 50 mm, 40 mm, 30 mm, 20 mm, 10 mm, 9 mm, 8 mm, 7 mm, 6 mm, 5 mm, 4 mm, 3 mm, 2 mm, or 1 mm. The slub may be any suitable length, such as, for example, 100 mm or less, such as for example, 50 mm, 45 mm, 40 mm, 35 mm, 30 mm, 25 mm, 20 mm, 15 mm, 10 mm, 5 mm, 4 mm, 3 mm, 2 mm, or 1 mm. The slub may be a percentage of the total discrete cord length, such as, for example, 50%, 45%, 40%, 35%, 30%, 25%, 20%, 15%, 10%, or 5%.

The cord supply may be wound around any volumetric shape wherein the cord makes the outer surface of the shape, such as, for example, a cone, a spool, a cylinder, or a bobbin. The cord supply may be wound around two fixed ends of a tangible shape. Alternatively, the cord supply may be layered such that it rests upon itself.

In a non-limiting configuration, the deployed cord supply is forced to contact the transfer member by one or more physical constraints, one or more intangible constraints, or combinations thereof. Without being bound by theory, it is believed that forcing the deployed cord supply to contact the transfer member allows for better discrete cord control by preventing the discrete cord from continuing to follow the fluid flow after it is separated from the deployed cord supply. Forcing the discrete cord to contact the transfer member enables the transfer member to transfer the discrete cord out of the fluid flow to the attachment system. The type of physical or intangible constraint may determine the distance that can be covered by the transfer member.

In a non-limiting configuration, the physical constraint comprises a tangible body capable of creating friction between the deployed cord supply or the discrete cord and the transfer member. The tangible body may be any suitable shape, such as, for example, a spring loaded wheel or a wheel made of a compliant material.

The tangible body may be located on the first surface of the transfer member, housed within the cutting apparatus immediately adjacent to the second edge of the cutting apparatus opening. The tangible body forms a nip causing the discrete cord to contact the first surface of the transfer member. In an exemplary configuration, the tangible body comprises a spring loaded wheel. The spring loaded wheel rotates at the velocity of the transfer member forcing the discrete cord against the first surface of the transfer member.

The tangible body may be located on the first surface of the transfer member outside of the cutting apparatus and immediately adjacent to the second edge of the cutting apparatus opening. In a non-limiting configuration, a plurality of tangible bodies may be used to maintain the discrete cord against the first surface of the transfer member until the discrete cord reaches the attachment system.

In a non-limiting configuration, an intangible constraint comprising one or more additional pressure sources may be used to force the deployed cord supply to contact the transfer member, creating friction between the deployed cord supply or the discrete cord and the transfer member. In an exemplary configuration, the intangible constraint may comprise a vacuum source within the transfer member enabled to create a vacuum against the first surface, second surface, or within the orifice of the transfer member.

In a non-limiting configuration, the transfer member may comprise an active clamp configured to grip the deployed cord supply or discrete cord inside the orifice of the transfer member. The active clamp may be spring loaded. The active clamp may force a portion of the discrete cord to contact an inner surface of the orifice. The active clamp may retract to release the discrete cord upon reaching the attachment system.

The apparatus may comprise a receiving chamber. The receiving chamber may comprise any suitable volumetric space comprising at least two openings to the volumetric space. In a non-limiting configuration, the receiving chamber has an opening comprising a first end wall, a second end wall, a bottom wall connecting the first end wall and the second end wall, and a top wall connecting the first end wall and second end wall. The receiving chamber may be tapered.

When deployed to vacuum, the receiving chamber comprises a back wall enclosing the receiving chamber and an opening to the vacuum source. The opening to the vacuum source may be located anywhere in the receiving chamber. The receiving chamber opening is formed by a first end wall, a second end wall, the bottom wall, and the top wall. The receiving chamber opening should be an area that allows for a continuous fluid flow through the transfer member. If the opening does not enable a continuous fluid flow, the fluid flow can pulse.

Alternatively, when deployed to vacuum, the receiving chamber may be any volumetric geometry provided that the opening to the receiving chamber comprises an opening with an arc-shaped slot, comprising a first end wall and a second end wall, whose radius is concentric and equal to the radius passing through the centers of the openings on the rim of the ring shaped transfer member. The arc-shaped slot may have a length equal to one pitch of the apertures on the transfer member plus or minus the width of an aperture.

The second end wall may comprise an outlet abutting the transfer member. The outlet may have a cross section area between 0.5 mm$^2$ to 30 mm$^2$. The outlet may pinch the discrete cord as it exits the receiving chamber by forcing it to come into contact with the rim of the second surface of the transfer member.

A tunnel may be joined to the receiving chamber at the outlet. Alternatively, a tunnel may be integral with the receiving chamber at the outlet. The integral tunnel may be a separate piece that connects to the opening of the receiving chamber and contacts the transfer member acting as the opening to the receiving chamber with a tunnel at the second end wall outlet. The tunnel can be of any suitable length such as, for example, 1 mm to 40 mm.

The receiving chamber may have a vacuum source. The vacuum source may draw between about 10 inches of water and about 80 inches of water, such as, for example, 30 inches of water, 35 inches of water, 40 inches of water, 45 inches of water, 50 inches of water, 55 inches of water, 60 inches of water, 65 inches of water, 70 inches of water, or 75 inches of water.

The attachment system may be any system capable of joining a discrete cord to a substrate. The attachment system is downstream of the supply path. The attachment system may abut the first surface or the second surface of the transfer member. The attachment system may abut the supply path. The attachment system may comprise any known means of attachment, such as, for example, a sewing apparatus, an adhesive, ultrasonics, heat, a stapling device, or combinations thereof.

The attachment system may be a sewing apparatus. The substrate may be moved along the stitch plate by a star wheel, by a set of protuberances on the transfer member rim, the sewing apparatus, and combinations thereof. The sewing apparatus may be configured to sew the discrete cord to a substrate by any number of desired stitches for a length of discrete cord.

The substrate may be a pledget. The pledget may comprise rayon, cotton, or combinations of both materials. These materials have a proven record of suitability for use in the human body. The rayon used in the absorbent material may be any suitable type typically used in disposable absorbent articles intended for in vivo use. Such acceptable types of rayon include GALAXY Rayon (a tri-lobed rayon structure) available as 6140 Rayon from Acordis Fibers Ltd., of Hollywall, England. SARILLE L Rayon (a round fiber rayon), also available from Acordis Fibers Ltd. is also suitable. Any suitable cotton material may be used in the absorbent material. Suitable cotton materials include, long fiber cotton, short fiber cotton, cotton linters, T-fiber cotton, card strips, and comber cotton. The cotton may be scoured and bleached cotton absorbent with a glycerin finish, or other suitable finish.

The pledget may comprise a first end, middle section, and a second end along a longitudinal axis. The first end may also correspond to the withdrawal end to which a withdrawal cord may be attached. The second end may also correspond to the insertion end. The pledget may comprise absorbent layers comprising absorbent fiber materials.

The pledget may be any suitable shape, size, material, or construction for compression or formation into a tampon having a vaginally insertable shape. The pledget may be generally square or rectangular or take on other shapes such as trapezoidal, triangular, hemispherical, chevron or hourglass shapes.

The pledget may be a laminar structure comprised of integral or discrete layers. The absorbent material may comprise 100% rayon fibers or 100% cotton fibers. The absorbent material may comprise a combination of rayon and cotton fibers in any suitable combination. The absorbent material may comprise greater than about 25%, 30% or 40% rayon fibers and the balance of the absorbent material comprising cotton fibers. The absorbent material may comprise greater than about 50% rayon fibers with cotton fibers comprising the balance of the absorbent material. The absorbent material may comprise greater than about 60, 70, 75, 80 or 90% rayon fibers and the balance of the absorbent material comprising cotton fibers. In one layered configuration, each of the layers may comprise essentially 100% of the same material, such as outer layers of 100% rayon and an intermediate layer of 100% cotton. A Super Plus absorbency tampon may be made from a pledget comprising about 100% rayon fibers. A Super absorbency or Regular absorbency tampon may be made from a pledget comprising about 25% cotton and about 75% rayon fibers. A Junior absorbency tampon may be made from a pledget comprising about 50% cotton and about 50% rayon fibers.

The pledget may be constructed from a wide variety of liquid-absorbing materials commonly used in absorbent articles such as rayon (including tri-lobal and conventional rayon fibers), cotton, or comminuted wood pulp which is generally referred to as airfelt. Examples of other suitable absorbent materials include, but are not limited to, creped cellulose wadding; meltblown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures thereof.

Typical absorbent materials may comprise cotton, rayon folded tissues, woven materials, nonwoven webs, synthetic and natural fibers, or sheeting. The pledget and any component thereof, may comprise a single material or a combination of materials. Additionally, superabsorbent materials, such as superabsorbent polymers or absorbent gelling and open-celled foam materials, may be incorporated into the tampon.

Examples of the absorbent fiber materials used for the absorbing layer include hydrophilic fibers such as cotton, rayon and synthetic fiber. Single or multiple fiber webs, nonwoven or woven fabrics, preferably having a weight of 150 g/m$^2$ to 1,500 g/m$^2$ and a thickness of substantially 0.1 mm to 0.9 mm are lapped over another absorbent fiber material to form an absorbing layer having a thickness of 1.0 mm to 15 mm and preferably having a thickness of 2.0 mm to 10 mm are used as the absorbing layer.

Fiber webs and nonwoven fabrics may be shaped by card webbing, air-laying method, wet laid method and the like, on a base such as a synthetic fiber sheet. Hydrophobic fibers or hydrophobic fibers comprising a hydrophilic property may also be comprised in the absorbing layer with the hydrophilic fibers. In addition, compounds having a water absorbing property, such as polymers with a high water absorbing property, may be comprised in the absorbing layer. The surface material with liquid permeability is made of nonwoven fabrics formed by hydrophobic fibers or mesh films, to which mesh treatment has been performed. The type of nonwoven fabrics used for the surface material is not particularly limited and examples include spunbond nonwoven fabrics, spunlace nonwoven fabrics and thermal bond nonwoven fabrics.

The hydrophobic fiber which makes up the nonwoven fabrics is not particularly limited and examples include fibers of polyester, polypropylene and polyethylene. The weight of the nonwoven fabrics is between 8 g/m² to 40 g/m².

A typical size for the pledget prior to compression may be from about 30 or 40 mm to about 60, 70, 80, 90 or 100 mm in length and from about 40 or 50 mm to about 70, 75, 80, 85, or 90 mm in width. The typical range for the overall basis weight may be from about 150, 200, or 250 gsm to about 600, 800, 1000 or 1100 gsm.

In a non-limiting configuration, a pledget may advance in a machine direction along a conveyor track to the sewing apparatus that engages the discrete cord. The pledget may be oriented such that the first end is perpendicular with the machine direction. In such a non-limiting configuration, the discrete cord sewing apparatus may be configured to sew a portion of a single discrete cord to the pledget. The sewn portion of the single discrete cord may be sewn along the longitudinal axis of the pledget in the first end of the pledget. Alternatively, the sewn portion of the single discrete cord may be sewn along the longitudinal axis of the pledget in the middle section. The single discrete cord extends beyond the pledget. The discrete cord may be sewn onto the pledget by one or more stitches, such as, for example, between 1 and 20 stitches, such as, for example, 2 stitches, 3 stitches, 4 stitches, 5 stitches, 6 stitches, 7 stitches, 8 stitches, 9 stitches, or 10 stitches.

The conveyor may comprise an infeed that places substrates, such as pledgets, on the conveyor. The conveyer and the infeed may be adjusted to space the pledgets apart based on the discrete cord setting. The conveyer may feed the pledget to a sewing apparatus. The conveyor may be timed so that the number of pledgets is timed with the number of discrete cords to have one pledget for every one discrete cord.

The metering system, transfer member, cutting apparatus, and conveyor may work in unison to deliver a discrete cord to a substrate. The metering system, transfer member, cutting apparatus, and conveyor may work in unison to deliver multiple discrete cords to a substrate. In a non-limiting configuration, the metering system, transfer member, cutting apparatus, and conveyor may be phased to control the location of the discrete cord on the substrate. Phasing the metering system, cutting apparatus, transfer member, and conveyor allows a discrete cord to be attached to a pledget within an acceptable error of a predetermined location on the pledget.

While the present disclosure discusses an apparatus for delivering a discrete cord to a pledget, it is to be appreciated that the methods and apparatuses disclosed herein may be used to deliver a cord to any form of substrate that has a discrete cord attached onto the substrate.

FIG. 1 shows a simplified flowchart of the apparatus 100. The apparatus 100 comprises a metered cord supply 200 and a supply path 300. The metered cord supply 200 comprises a cord supply 210 and a metering system 220. The supply path 300 comprises a cutting apparatus 500 and a transfer member 400. The apparatus 100 may further comprise a receiving chamber 700. As shown in FIG. 1, a pressure source 205 may be placed between the metered cord supply 200 and the supply path 300, after the receiving chamber 700, or in both locations. The transfer member 400 moves out of the supply path 300 towards an attachment system 800.

Figure 2A:
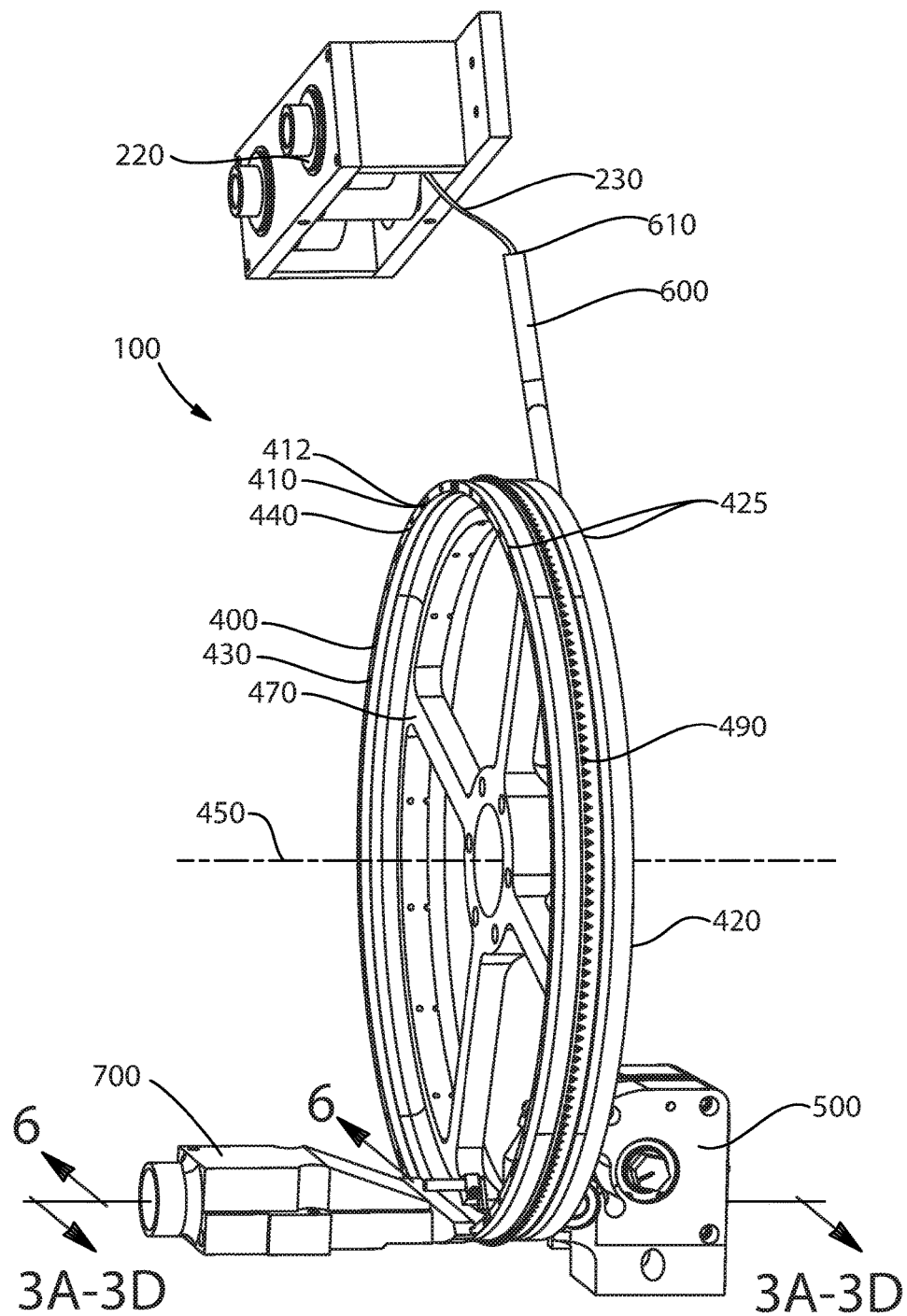
FIG. 2A is a perspective view of the apparatus.
Figure 2B:
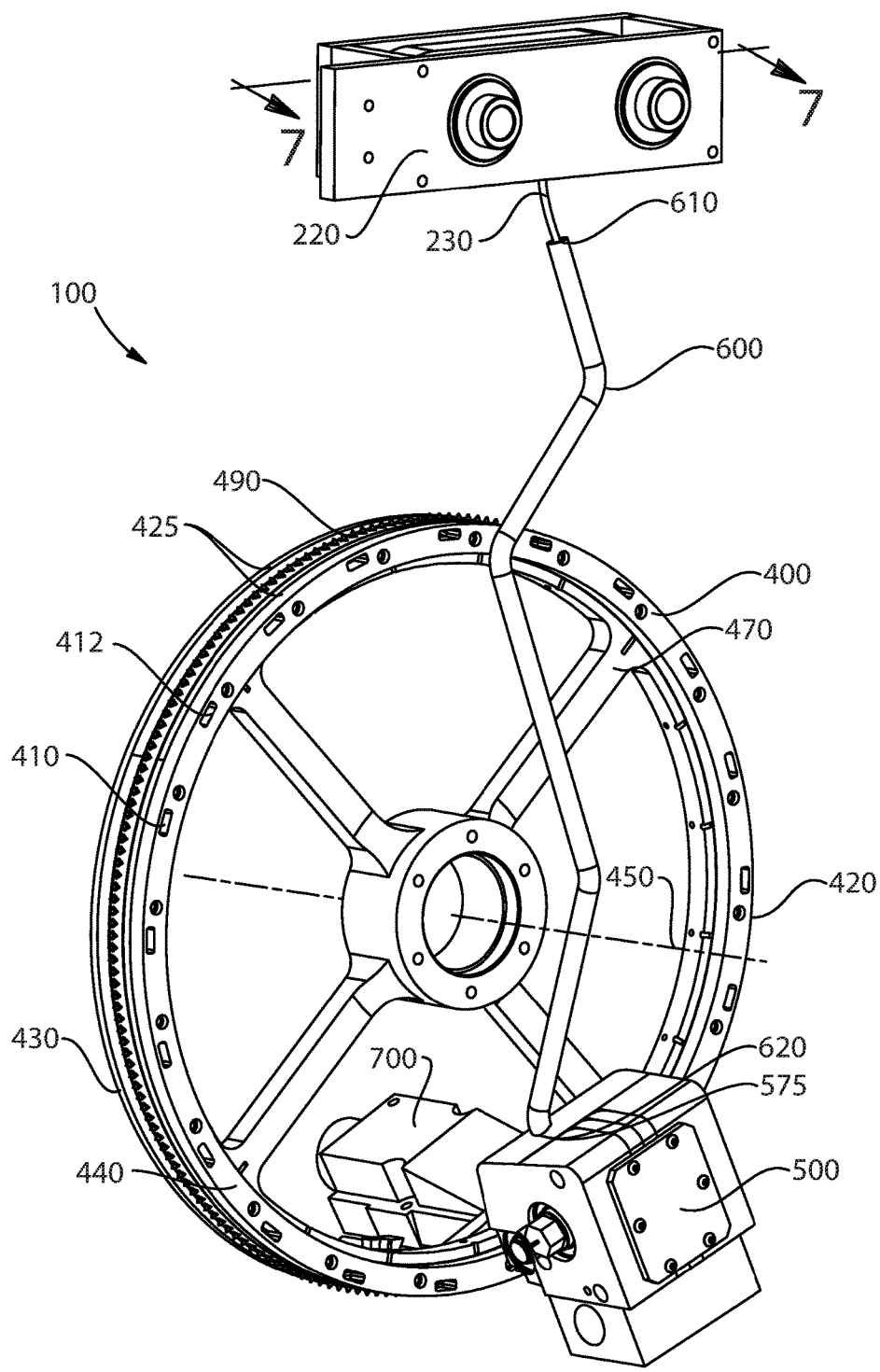
FIG. 2B is a perspective side view of the apparatus of 2A.

FIGS. 2A-B show an exemplary configuration of the apparatus 100. The apparatus 100 comprises a transfer member 400 connected to a cutting apparatus 500. The cutting apparatus 500 is connected to a transfer tube 600. The transfer tube 600 is connected to a metering system 220. The transfer member 400 rotates about a central axis 450. A receiving chamber 700 abuts the transfer member 400.

The transfer member 400 comprises a plurality of orifices 412 in the form of apertures 410 that connect a first surface of the transfer member 420 to a second surface of the transfer member 430. The distance between the first surface 420 and the second surface 430 may equal the width 425 of the transfer member 400. The apertures 410 are located within a rim 440 of the transfer member 400. The transfer member apertures 410 are equidistant. The transfer member 400 may comprise one or more protuberances 490 that extend beyond the circumference of the rim 440. The protuberances 490 may engage with a substrate to help move the substrate.

The transfer member 400 may comprise one or more spokes 470 connecting the transfer member rim 440 to a central axis 450. The transfer member 400 may rotate in either a clockwise or counter clockwise direction.

The transfer tube 600 comprises an inlet 610 connected to the metering system 220 and an outlet 620 (not shown in FIG. 2A) that is in direct contact with an inlet 575 of the cutting apparatus 500. The transfer tube 600 inlet 610 may be partially open to the atmosphere. The deployed cord supply 230 enters the transfer tube 600 at the inlet 610.

FIGS. 3A-D show a development of the stepped cross sectional view resulting from section line 3-3 of FIG. 2A. FIGS. 3A-D show the cutting apparatus 500, the transfer member 400, and the receiving chamber 700. The transfer member 400 comprises a first surface 420, a second surface 430, and orifices 412 in the form of apertures 410 that are equidistant within the rim 440. The cutting apparatus 500 comprises an opening 540 made up of a first edge 520, a second edge 530, a bottom wall 525 connecting the first edge 520 and the second edge 530, and a top wall (not shown) connecting the first edge 520 and the second edge 530. The cutting apparatus 500 comprises a knife 510 configured to sever a portion of the deployed cord supply 230 into a discrete cord 900. The knife 510 rotates along an alternative fluid flow path 555 formed by a gap between the rotary axis 550 for the knife 510 and the casing 560 for the knife 510. The knife 510 is rotated about a rotary axis 550 and bisects the fluid flow 310 of the deployed cord supply 230 while contacting a pressure surface 515. The alternate fluid flow path 555 maintains a fluid flow 310 when the knife 510 bisects the deployed cord supply 230. The opening 540 to the cutting apparatus 500 is in direct contact with the first surface 420 of the transfer member 400.

The receiving chamber 700 comprises a first end wall 720, a second end wall 730, a lower wall 725 connecting the first end wall 720 and the second end wall 730, and a upper wall (not shown) connecting the first end wall 720 and the second end wall 730. A receiving chamber comprises an opening 740 which is in direct contact with the second surface 430 of the transfer member 400. The receiving chamber 700 second end wall 730 comprises an outlet 750 that abuts the transfer member 400. The receiving chamber 700 may comprise an outlet 750 and a tunnel 755.

Figure 3A:
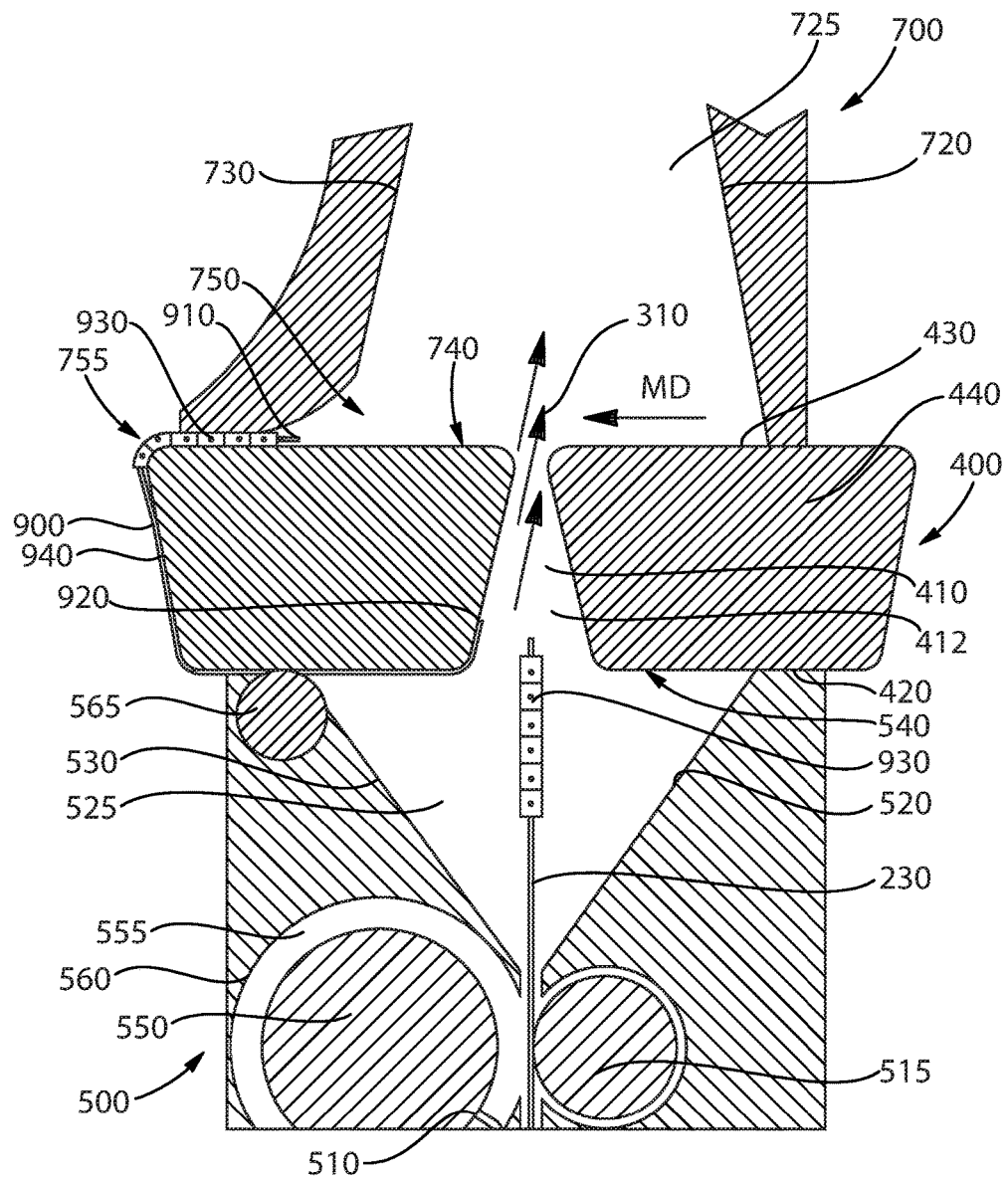
FIG. 3A is a cross section view of a portion of the apparatus taken along 3-3 of FIG. 2A.
Figure 3B:
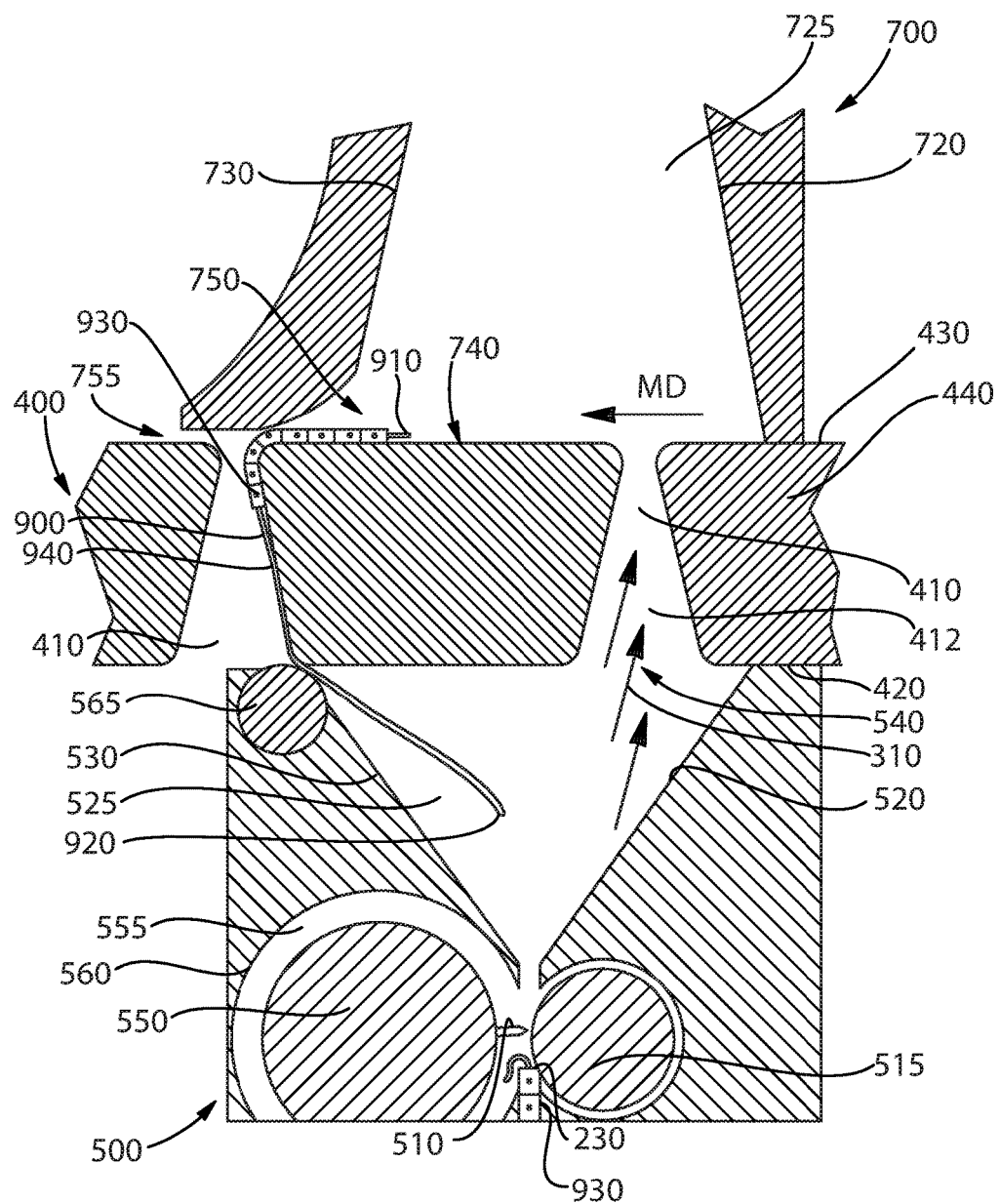
FIG. 3B is a cross section view of a portion of the apparatus taken along 3-3 of FIG. 2A.
Figure 3C:
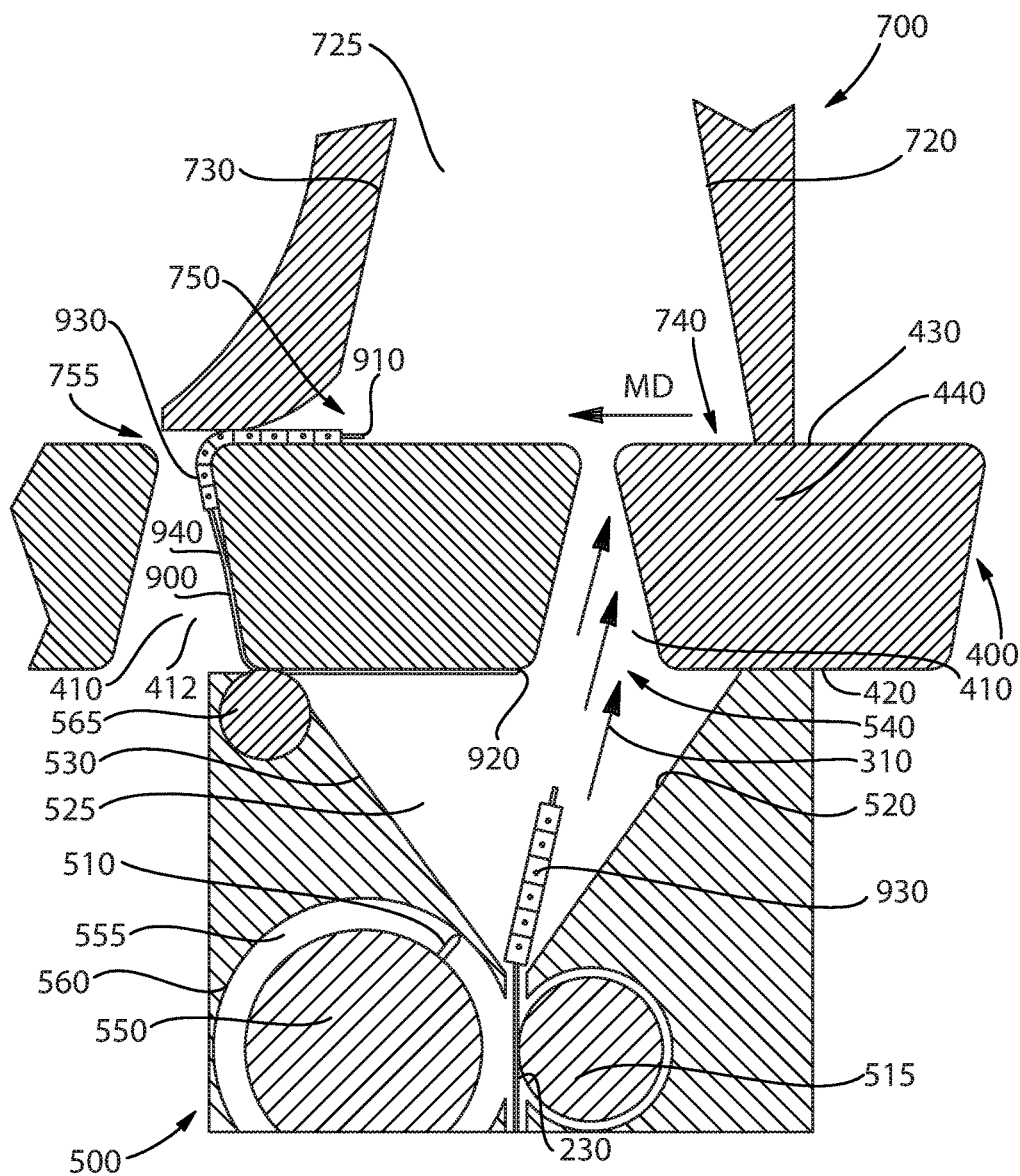
FIG. 3C is a cross section view of a portion of the apparatus taken along 3-3 of FIG. 2A.
Figure 3D:
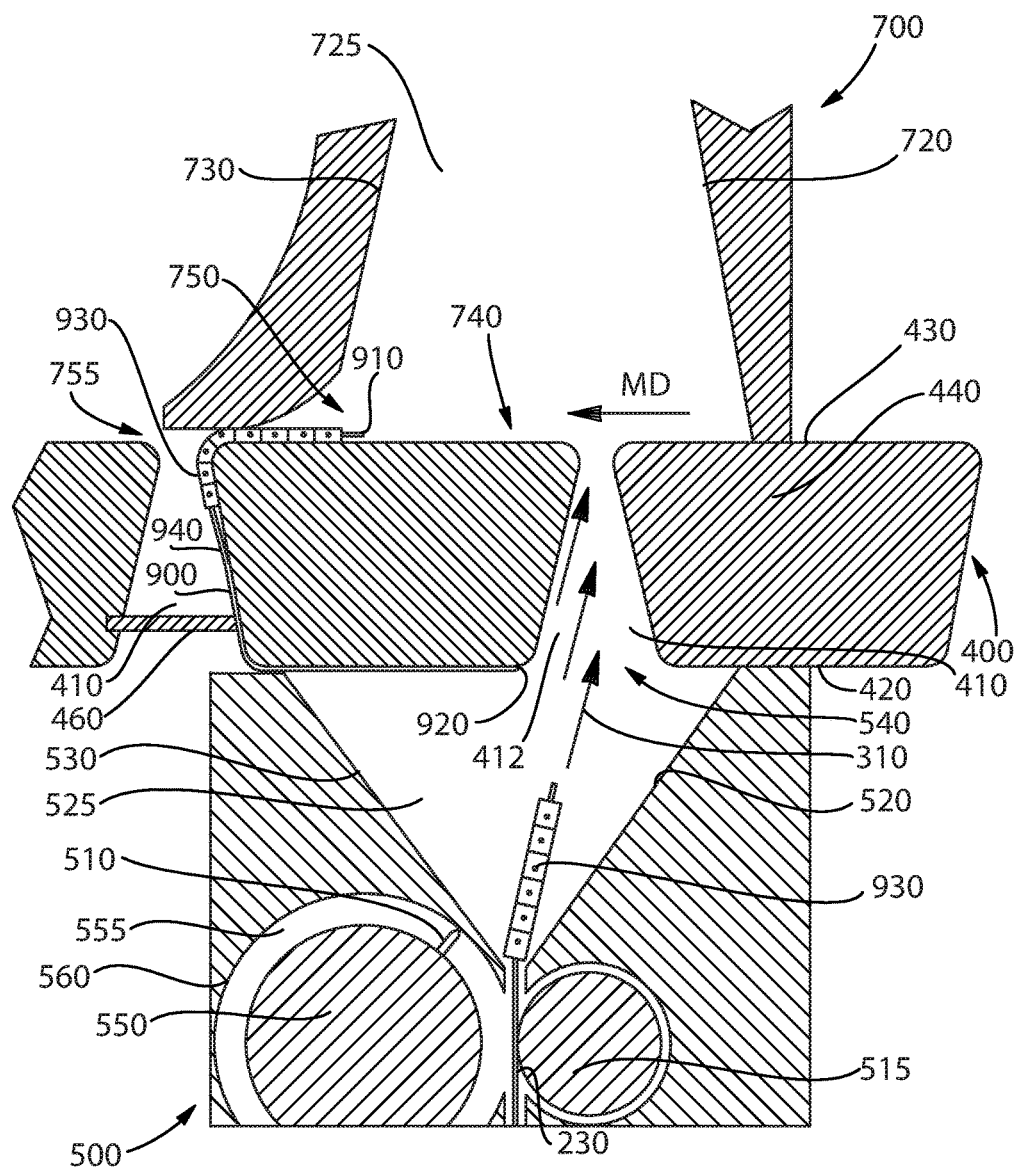
FIG. 3D is a cross section view of a portion of the apparatus taken along 3-3 of FIG. 2A.

FIGS. 3A-C illustrate three snapshots of how the apparatus creates and delivers a discrete cord 900. As shown in FIGS. 3A-C, an aperture 410 of the transfer member 400 receives a discrete cord 900 as it moves through the fluid flow 310 in a Machine Direction. As shown in FIGS. 3A-C, the cutting apparatus 500 second end wall 530 may comprise a tangible body 565. Alternatively, as shown in FIG. 3D, the transfer member 400 may comprise an active clamp 460.

The discrete cord 900 is a predetermined length. The discrete cord 900 has a first end 910 and a second end 920. The predetermined length may comprise a slub 930 and a non-slub portion 940. Alternatively, the cord supply may comprise a continuous cord that consists only of a non-slub portion 940. The slub 930 may be made of the same material as the rest of the cord or of a different material.

As shown in FIG. 3A, a transfer member aperture 410 enters the fluid flow 310 while another transfer member aperture 410 exits the fluid flow 310 with a discrete cord 900. The entering transfer member aperture 410 maintains the fluid flow 310 creating a path for the deployed cord supply 230.

As shown in FIG. 3B, a tangible body 565 deflects the deployed cord supply 230 against the transfer member 400 concurrent with a knife 510 cutting the deployed cord supply 230 to form a discrete cord 900. The discrete cord 900 first end 910 crosses through the transfer member aperture 410 and enters the receiving chamber 700. The discrete cord 900 first end 910 is deflected towards the second surface 430 of the transfer member 400 by the outlet 750 in the receiving chamber 700. The transfer member aperture 410 moves between the cutting apparatus 500 and the receiving chamber 700 through the fluid flow 310. The knife 510 bisects the fluid flow 310 and the deployed cord supply 230 may follow the alternate fluid flow path 555 of the cutting apparatus 500.

As shown in FIG. 3C, the discrete cord 900 has a first end 910 and a second end 920. The transfer member aperture 410 has begun exiting the fluid flow 310 with a discrete cord 900 that is in contact with the tangible body 565 and the first surface 420 of the transfer member 400. An aperture 410 has entered the fluid flow 310. The deployed cord supply 230 follows the fluid flow 310 towards the aperture 410 while the knife 510 rotates along the alternative fluid flow path 555 formed by a gap between the rotary axis 550 for the knife 510 and the casing 560 for the knife 510. One of ordinary skill in the art would comprehend that FIGS. 3A-C represent a portion of a transfer member which may comprise a plurality of equidistant apertures or, alternatively, segments comprising apertures which are connected in a closed chain such that a first segment will be reintroduced into the system after the last segment of the transfer member.

Alternatively, as shown in FIG. 3D, the discrete cord 900 may be held inside of the aperture 410 by an active clamp 460.

Figure 4A:
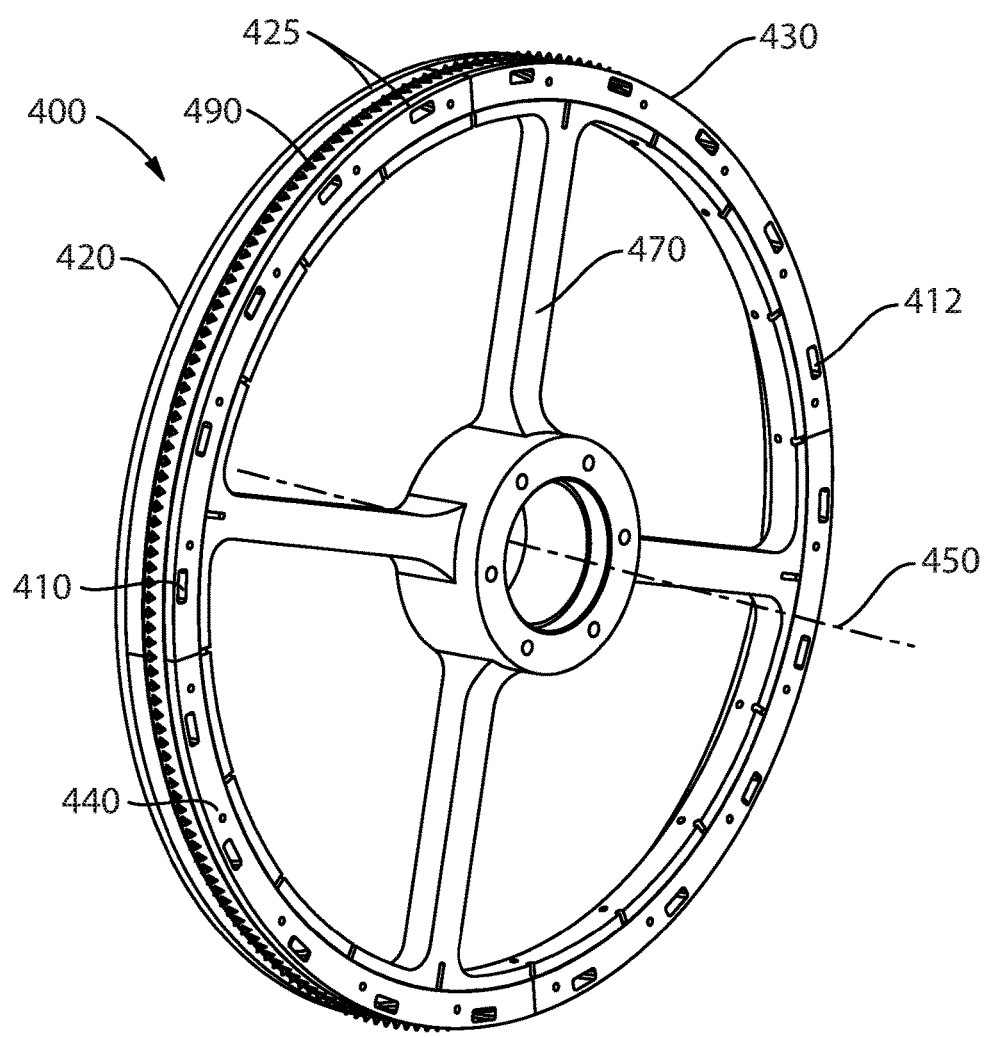
FIG. 4A is a perspective view of a transfer member.
Figure 4B:
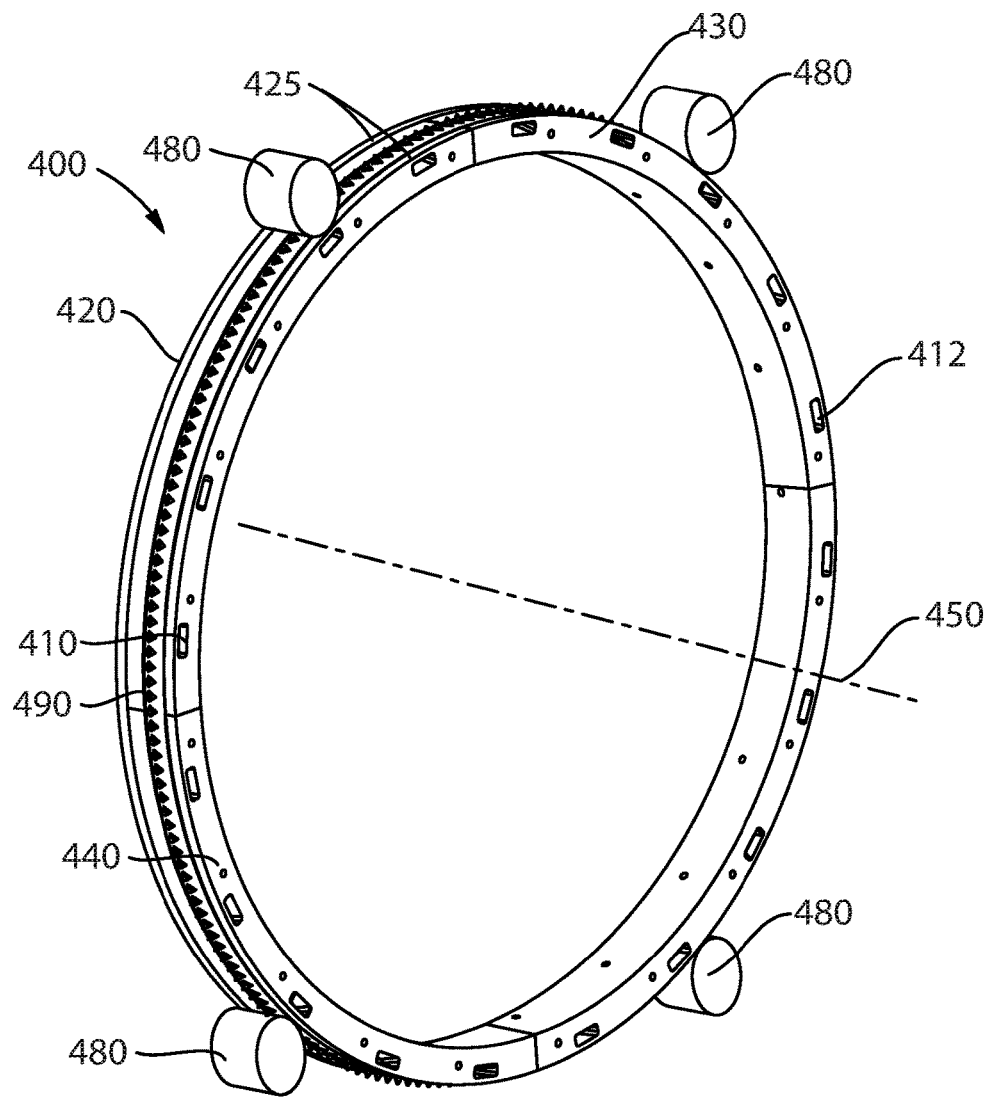
FIG. 4B is a perspective view of a transfer member.
Figure 4C:
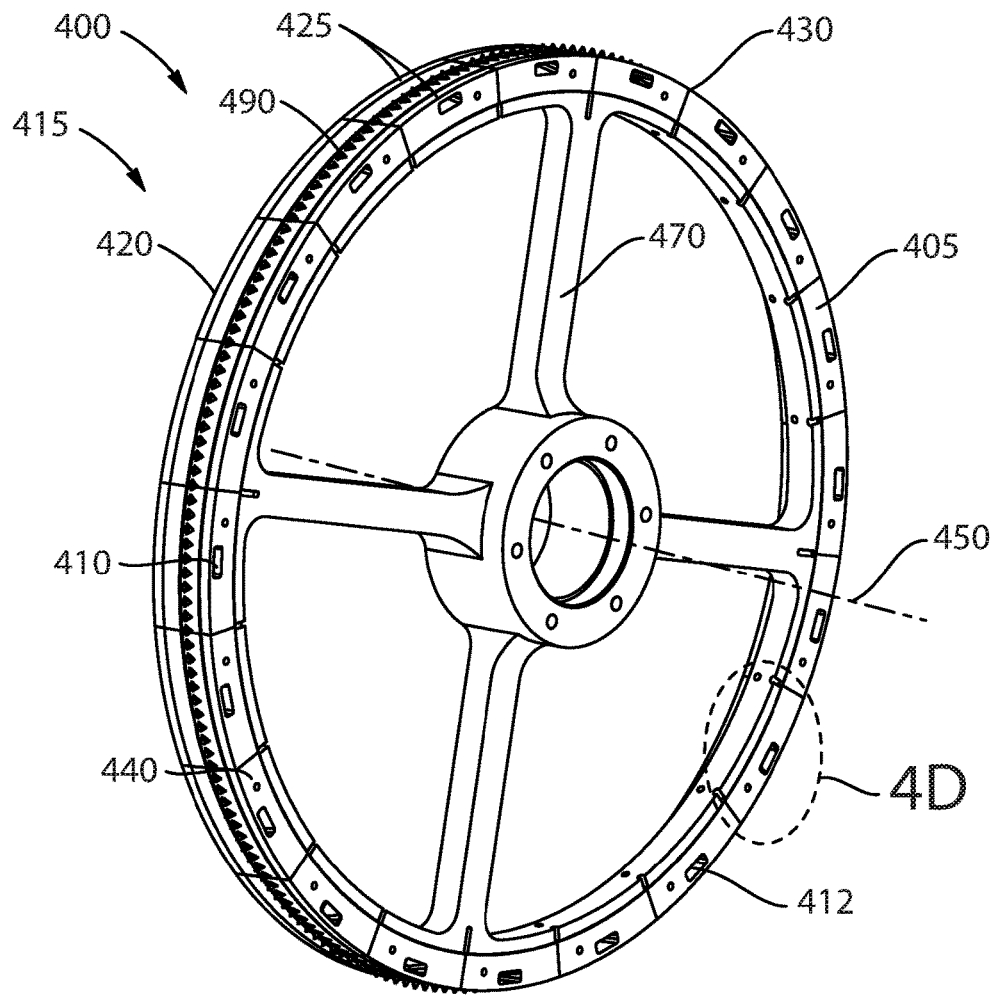
FIG. 4C is a perspective view of a transfer member comprising segments.

FIGS. 4A-E show exemplary representations of transfer members 400. As shown in FIGS. 4A-C, the transfer member 400 comprises a plurality of orifices 412 in the form of apertures 410 that cross through the first surface 420 of the transfer member rim 440 to the second surface 430 of the transfer member rim 440. The distance between the first surface 420 and the second surface 430 may equal the width 425 of the transfer member 400. Protuberances 490 may extend beyond the circumference of the transfer member rim 440. The transfer member 400 rotates about a central axis 450.

As shown in FIG. 4A, the transfer member 400 may comprise one or more spokes 470 connecting the transfer member rim 440 to a central axis 450. As shown in FIG. 4B, the transfer member 400 may comprise a rim 440 with a central axis 450 held by three or more support wheels 480. Four support wheels 480 may hold the transfer member in place in a square configuration. Three support wheels 480 may hold the transfer member 400 in place in a triangle configuration (not shown).

FIG. 4C shows a transfer member 400 comprising a plurality of segments 405, wherein each of the segments 405 comprise an orifice 412 in the form of an aperture 410. The transfer member 400 comprises one or more spokes 470 connecting the transfer member rim 440 to a central axis 450. The closed chain 415 may be in the form of a ring. Alternatively, it shall be understood that the closed chain 415 may be serpentine (not shown).

Figure 4D:
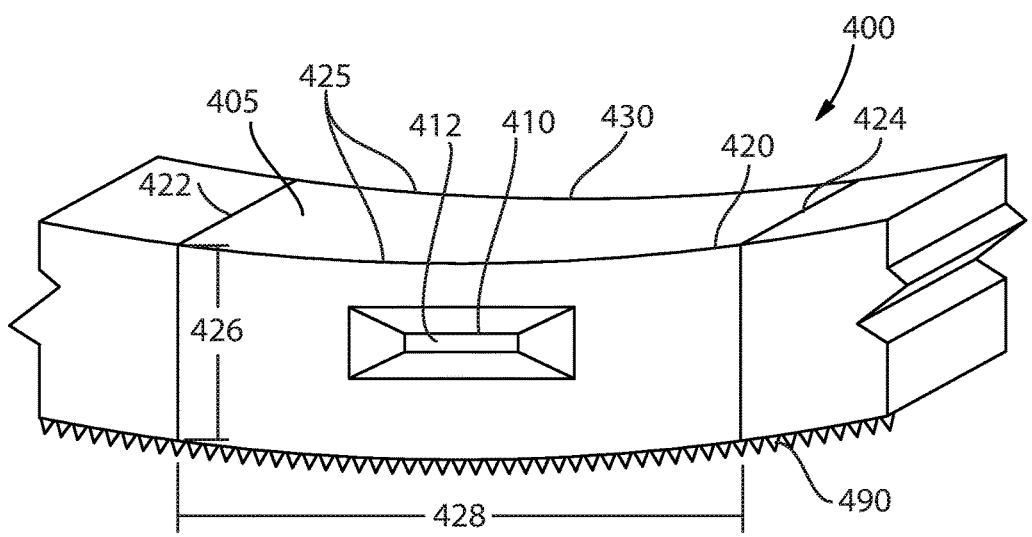
FIG. 4D is a close up view of a transfer member segment from FIG. 4C.

FIG. 4D shows a close up perspective view of a transfer member segment 405 of FIG. 4C. The segment 405 comprises a first surface 420, a second surface 430, a front end 422, a back end 424, a width 425 defined by the distance between the first surface 420 and the second surface 430, a height 426, and a length 428. The segment 405 comprises an orifice 412 in the form of an aperture 410 connecting the first surface 420 with the second surface 430. The segment 405 may comprise protuberances 490 extending radially outward from the segment 405.

Figure 4E:
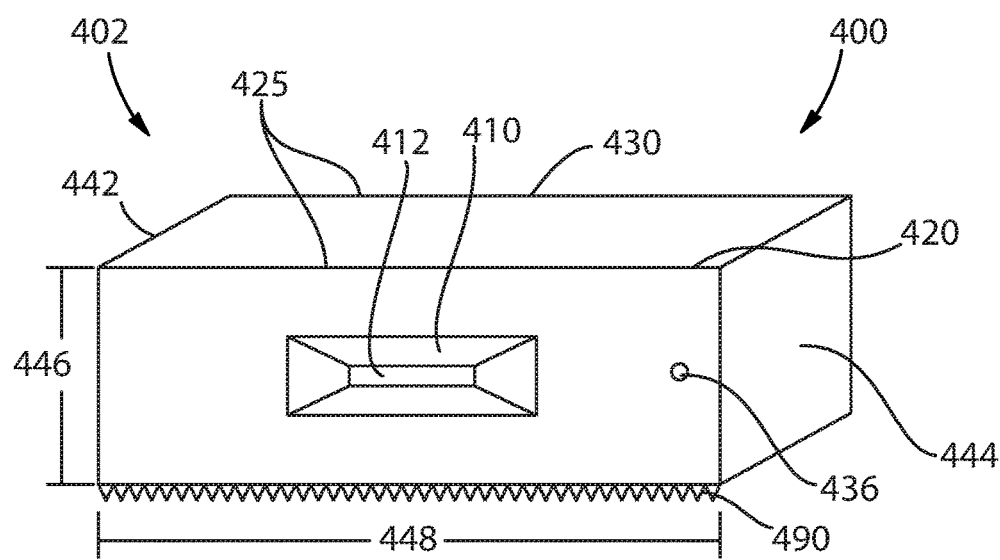
FIG. 4E is a perspective view of a transfer member.

FIG. 4E shows a transfer member 400 comprising a body 402 with one aperture 410. The body 402 comprises a first surface 420, a second surface 430, a front end 442, a back end 444, a width 425 defined by the distance between the first surface 420 and the second surface 430, a height 446, and a length 448. The body 402 comprises an orifice 412 in the form of an aperture 410 connecting the first surface 420 with the second surface 430. The body 402 may comprise a hole 436 that connects the first surface 420 with the second surface 430. The body 402 may comprise protuberances 490 extending radially outward from the body 402.

Figure 5A:
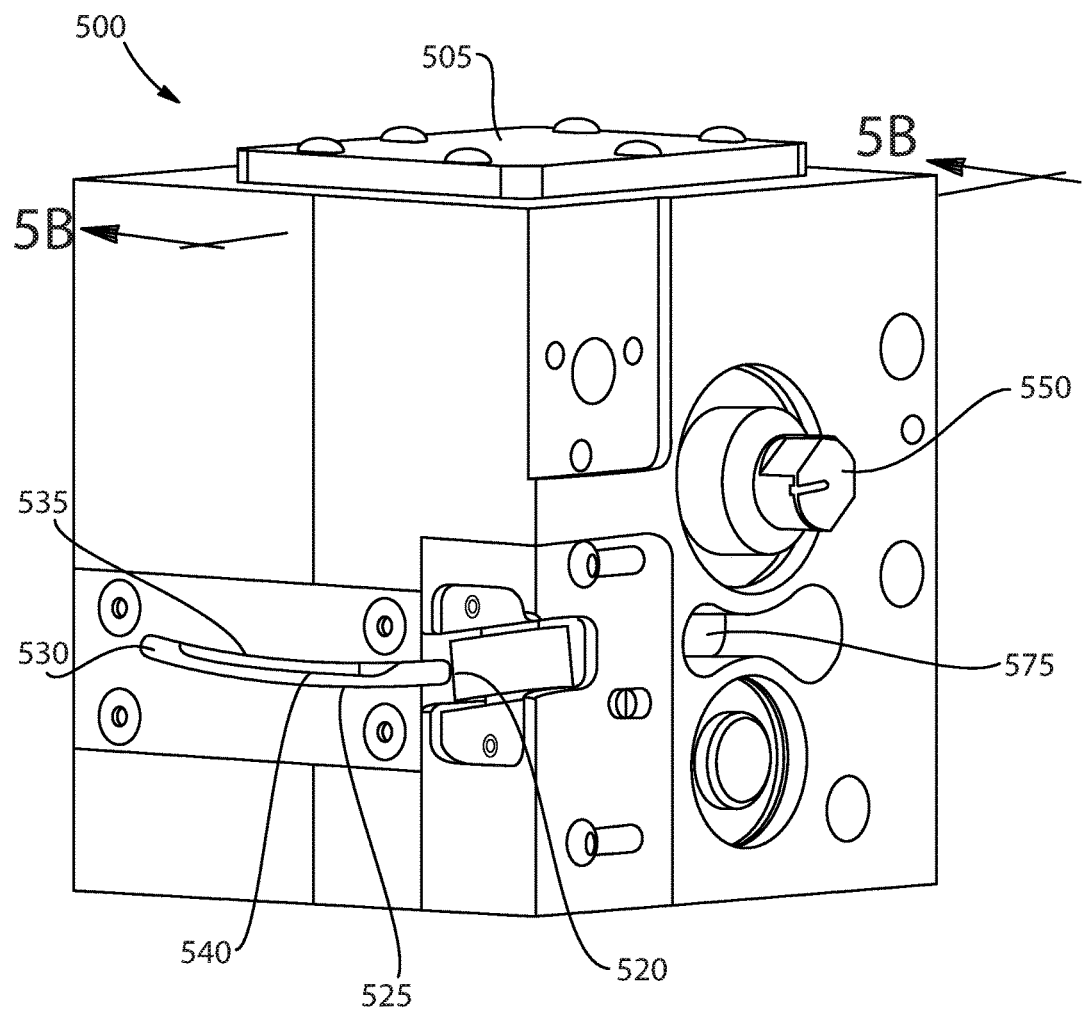
FIG. 5A is a perspective view of a cutting apparatus.
Figure 5B:
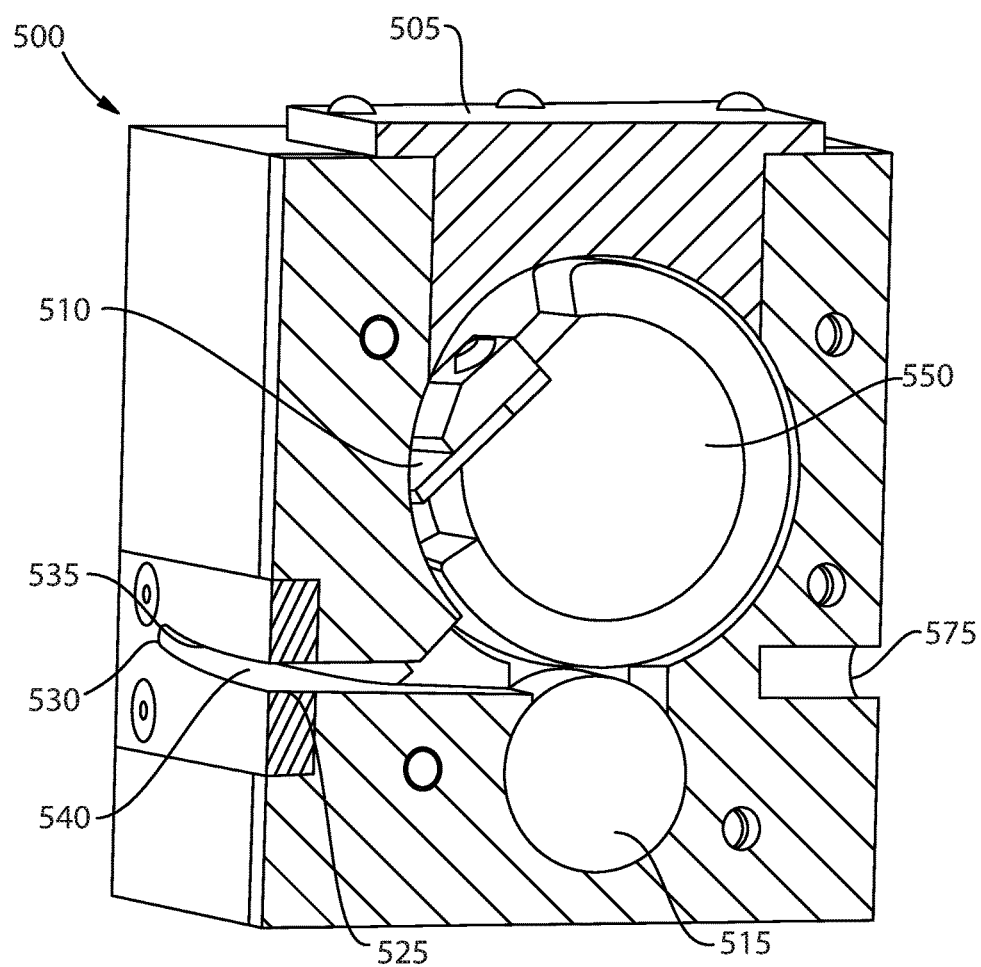
FIG. 5B is a cross section view of the cutting apparatus of FIG. 5A taken along 5-5.

FIGS. 5A and 5B show an exemplary configuration for the cutting apparatus 500. FIG. 5A is a perspective view of the cutting apparatus 500. FIG. 5B is a sectional view of the cutting apparatus 500 along 5-5 of FIG. 5A. The cutting apparatus 500 of FIGS. 5A and 5B comprises a rotary axis 550 within a housing 505. The housing 505 comprises an inlet 575 and an opening 540 to the cutting apparatus 500. The opening 540 to the cutting apparatus 500 comprises a first edge 520 (not shown in FIG. 5B) and a second edge 530 that are connected by a bottom wall 525 and an upper wall 535.

FIG. 5B is a sectional view of the cutting apparatus 500 along 5-5 of FIG. 5A. The cutting apparatus 500 comprises a rotary axis 550 about which a knife 510 rotates. The cutting apparatus 500 further comprises a pressure surface 515. The opening 540 to the cutting apparatus 500 may match the opening to the receiving chamber in terms of total surface area.

Figure 6:
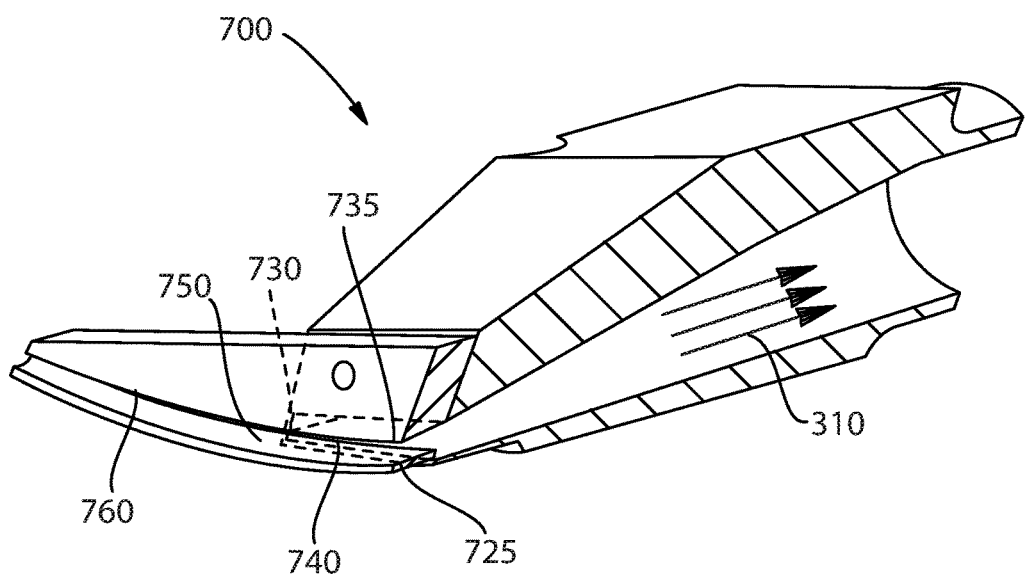
FIG. 6 is a perspective cross section view of the receiving chamber taken along 6-6 of FIG. 2A.

FIG. 6 shows a cross section of an exemplary receiving chamber 700 along line 6-6 of FIG. 2A. The receiving chamber 700 has an opening 740 and a vacuum source creating the fluid flow 310. The opening comprises a second end wall 730, an upper wall 735 connecting a first end wall (not shown) to the second end wall 730, and a lower wall 725 connecting the first end wall (not shown) in the figure to the second end wall 730. The second end wall 730 of the receiving chamber 700 comprises an outlet 750. A tunnel 760, integral to the receiving chamber 700, extends beyond the second end wall 730.

Figure 7:
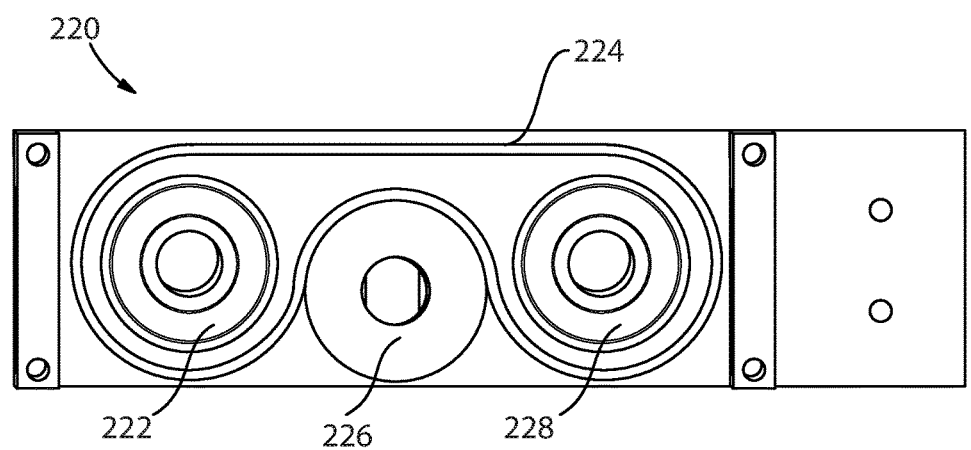
FIG. 7 is a cross section view of a metering system taken along 7-7 of FIG. 2B.

FIG. 7 shows a side elevation view of a metering system 220. The metering system 220 may be an apron roll. The apron roll may comprise a drive wheel 222, a belt 224, wrap wheel 226, and an idler wheel 228.

Figure 8:
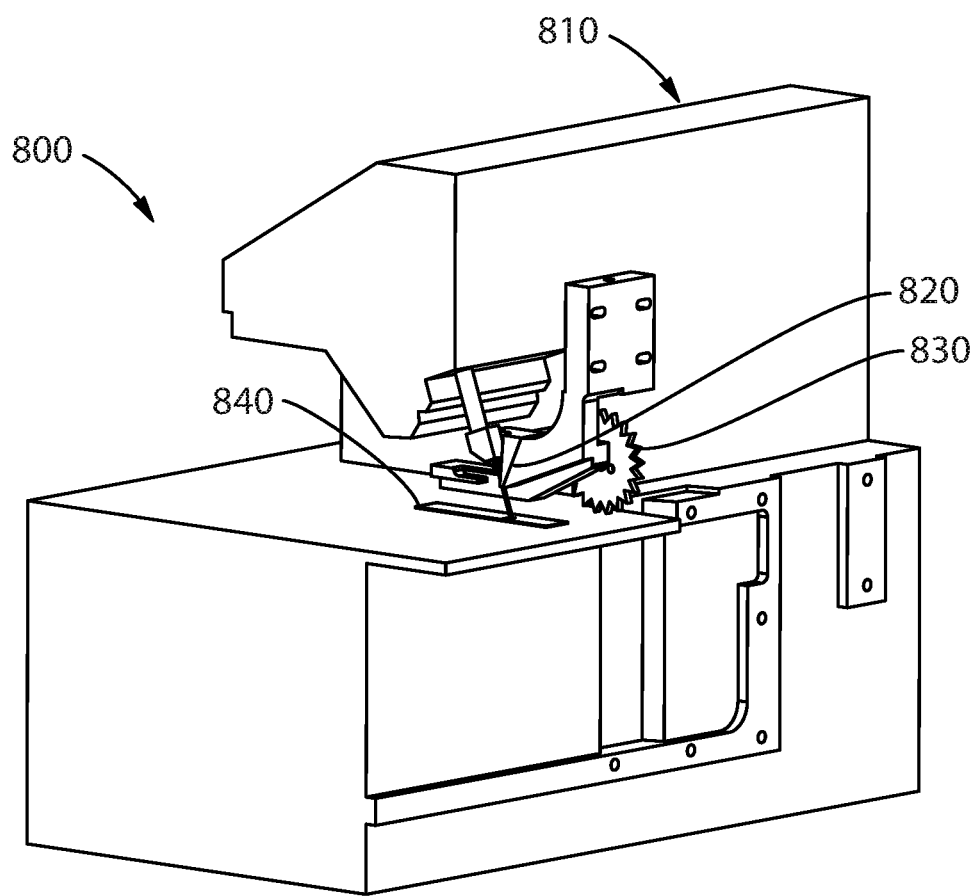
FIG. 8 is a perspective view of an attachment system.

FIG. 8 shows an attachment system 800 in the form of a sewing apparatus 810. The sewing apparatus 810 comprises a sewing needle 820 and a stitch plate 840 that runs along a machine direction. A feed wheel 830 is located above the stitch plate 840 configured to engage with the substrate. The feed wheel 830 may be in the form of a star wheel. The stitch plate 840 is directly under the sewing needle 820.

Figure 9:
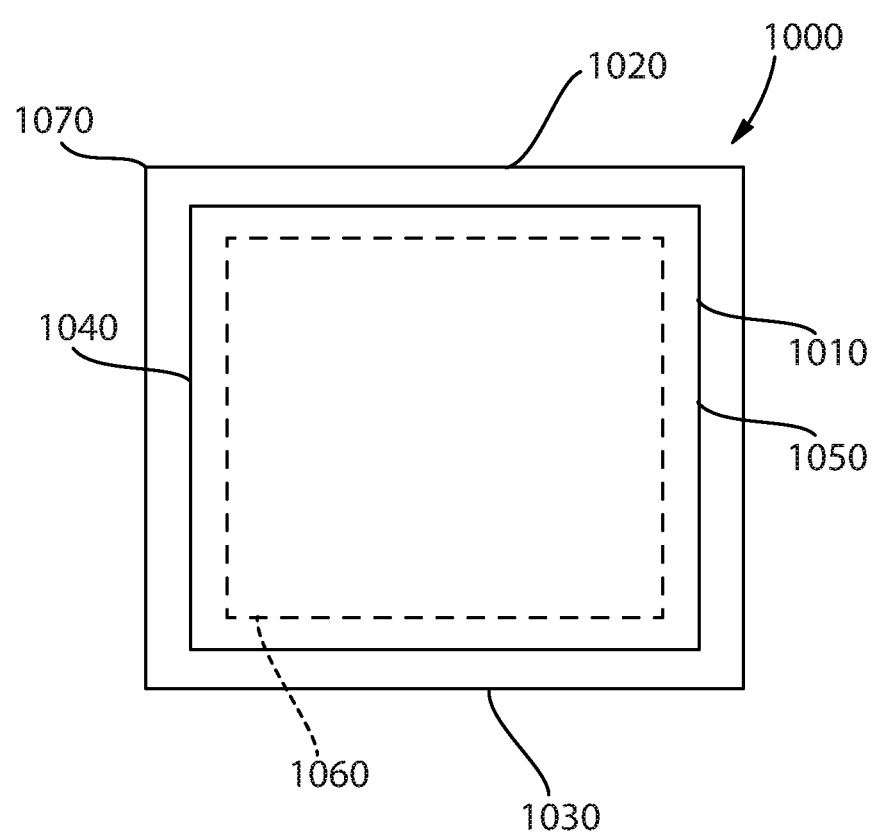
FIG. 9 exemplifies a pledget in a flat-out, uncompressed state.

FIG. 9 exemplifies a tampon pledget 1000 in a flat-out, uncompressed state. The absorbent material 1010 may form a tampon pledget 1000. The tampon pledget 1000 comprises an insertion end 1020, a withdrawal end 1030, a first longitudinal edge 1040, and a second longitudinal edge 1050. Compression of a tampon pledget 1000 can form a compressed absorbent member. The pledget 1000 can have an overwrap 1060 and an additional optional second overwrap 1070.

Figure 10:
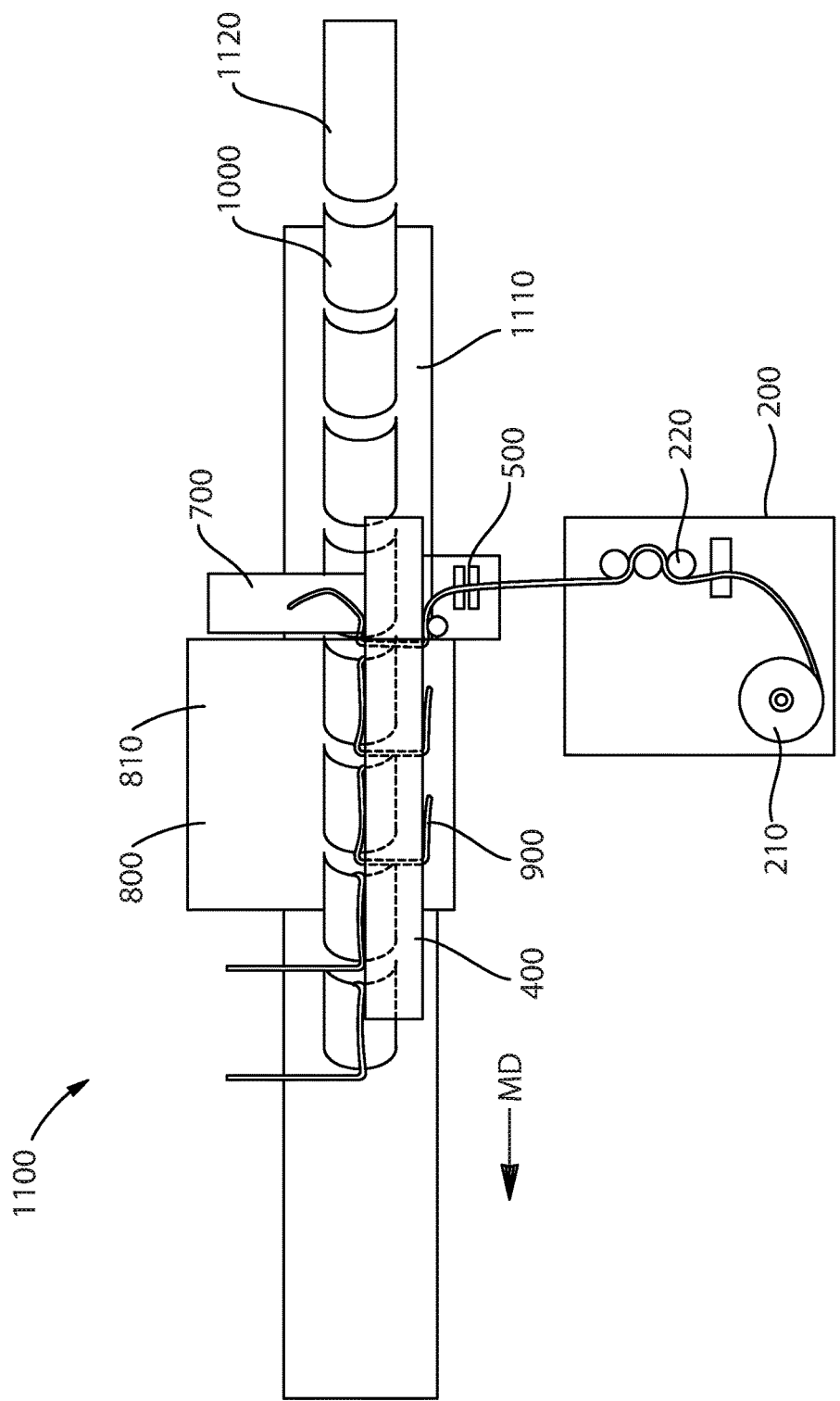
FIG. 10 is a schematic representation of the apparatus with an attachment system and a conveyor.

FIG. 10 shows a schematic representation of a potential process 1100. The schematic representation shows a conveyor 1110, a conveyor infeed 1120 capable of placing pledgets 1000 on the conveyor 1110, a metered cord supply 200 including a cord supply 210 and a metering system 220, a cutting apparatus 500, a transfer member 400, a receiving chamber 700, and an attachment system 800. As shown in FIG. 10, a conveyor infeed 1120 places chevron shaped pledgets 1000 on the conveyor 1110. The pledgets 1000 move in the Machine Direction (MD) on the conveyor 1110 towards the transfer member 400. The transfer member 400 receives a discrete cord 900 and moves the discrete cord 900 to the attachment system 800 or sewing apparatus 810 where it is joined to a pledget 1000. Each pledget 1000 receives one discrete cord 900.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. An apparatus for delivering a discrete cord, the apparatus comprising:
    a supply path comprising a fluid flow, a deployed cord supply, a transfer member having a first surface comprising one or more orifices capable of receiving the deployed cord supply, and a cutting apparatus comprising a cutting implement enabled to sever the deployed cord supply to form a discrete cord;
    wherein the fluid flow directs the deployed cord supply towards the transfer member first surface;
    wherein the transfer member first surface abuts the cutting apparatus;
    wherein the transfer member comprises a plurality of segments forming a closed chain; and
    wherein the apparatus further comprises a tangible body that creates friction between the deployed cord supply and the transfer member to deflect the deployed cord to transfer member first surface.

2. The apparatus of claim 1, wherein each segment of the plurality of segments comprises an orifice.

3. The apparatus of claim 1, wherein the plurality of segments form a rigid structure.

4. The apparatus of claim 3, wherein the transfer member rotates about a central axis.

5. The apparatus of claim 1, wherein the cutting apparatus comprises an alternative fluid flow path.

6. The apparatus of claim 1, wherein the apparatus comprises a metered cord supply comprising a metering system and a cord supply; wherein the metering system controls the rate at which the cord supply is deployed into the supply path.

7. The apparatus of claim 6, wherein the metering system is configured to coordinate with the transfer member and the cutting apparatus to deliver one discrete cord to each orifice of the transfer member.

8. An apparatus for delivering a discrete cord, the apparatus comprising:
    a supply path comprising a fluid flow, a deployed cord supply, a transfer member having a first surface comprising one or more orifices capable of receiving the deployed cord supply, and a cutting apparatus comprising a cutting implement enabled to sever the deployed cord supply to form a discrete cord;
    wherein the fluid flow directs the deployed cord supply towards the transfer member first surface;
    wherein the transfer member first surface abuts the cutting apparatus;
    wherein the transfer member comprises a body with an aperture enabled to reciprocate along a line or arc that moves the aperture through the fluid flow; and
    wherein the cutting apparatus comprises an alternative fluid flow path.

9. The apparatus of claim 8, wherein the apparatus further comprises a tangible body that creates friction between the deployed cord supply and the transfer member to deflect the deployed cord to transfer member first surface.

10. The apparatus of claim 8, wherein the apparatus comprises a metered cord supply comprising a metering system and a cord supply; wherein the metering system controls the rate at which the cord supply is deployed into the supply path.

11. The apparatus of claim 10, wherein the metering system is configured to coordinate with the transfer member and the cutting apparatus to deliver one discrete cord to each orifice of the transfer member.

12. An apparatus for delivering a discrete cord, the apparatus comprising:
    a supply path comprising a fluid flow, a deployed cord supply, a transfer member having a first surface comprising one or more orifices capable of receiving the deployed cord supply, and a cutting apparatus comprising a cutting implement enabled to sever the deployed cord supply to form a discrete cord;
    wherein the fluid flow directs the deployed cord supply towards the transfer member first surface;
    wherein the transfer member first surface abuts the cutting apparatus;
    wherein the transfer member comprises a plurality of segments forming a rigid structure; and wherein the apparatus further comprises a tangible body that creates friction between the deployed cord supply and the transfer member to deflect the deployed cord to transfer member first surface.

13. The apparatus of claim 12, wherein each segment of the plurality of segments comprises an orifice.

14. The apparatus of claim 12, wherein the transfer member rotates about a central axis.

15. The apparatus of claim 12, wherein the cutting apparatus comprises an alternative fluid flow path.

16. The apparatus of claim 12, wherein the apparatus comprises a metered cord supply comprising a metering system and a cord supply; wherein the metering system controls the rate at which the cord supply is deployed into the supply path.

17. The apparatus of claim 16, wherein the metering system is configured to coordinate with the transfer member and the cutting apparatus to deliver one discrete cord to each orifice of the transfer member.

\* \* \* \* \*